US005958705A

United States Patent [19]
Staunton et al.

[11] Patent Number: 5,958,705
[45] Date of Patent: Sep. 28, 1999

[54] CYTOPLASMIC MODULATORS OF INTEGRIN REGULATION/SIGNALING

[75] Inventors: Donald E. Staunton, Kirkland; Brian P. Lispky, Seattle, both of Wash.

[73] Assignee: ICOS Corporation, Bothell, Wash.

[21] Appl. No.: 08/839,581

[22] Filed: Apr. 15, 1997

Related U.S. Application Data

[63] Continuation-in-part of application No. 08/632,247, Apr. 15, 1996.
[51] Int. Cl.$^6$ ........................ G01N 33/566; G01N 33/53; C12N 15/12; C12N 5/10
[52] U.S. Cl. ........................ 435/7.1; 435/7.2; 435/325; 435/69.1; 530/350; 530/300; 536/23.5; 536/23.1
[58] Field of Search ........................ 435/7.1, 7.2, 69.1, 435/325; 530/350, 300; 536/23.1, 23.5

[56] References Cited

U.S. PATENT DOCUMENTS

| 5,561,047 | 10/1996 | Shattil | 435/7.21 |
| 5,587,166 | 12/1995 | Donachie | 424/255.1 |

OTHER PUBLICATIONS

Liu et al., Cloning and sequencing of a human cDNA from cytolytic NK/T cells with homology to yeast SEC7, Biochimica Biophysica Acta., 1132: 75–78, 1992.
Altschul et al., "Basic Local Alignment Search Tool," *J. Mol. Biol.,* 215:403–410 (1990).
Baron et al., "Surface Expression of α4 Integrin by CD4 T Cells Is Required for Their Entry into Brain Parenchyma," *J. Exp. Med.,* 177:57–68 (1993).
Baron et al., "The Pathogenesis of Adoptive Murine Autoimmune Diabetes Requires an Interaction between α4–Integrins and Vascular Cell Adhesion Molecule–1," *J. Clin. Invest.,* 93:1700–1708 (1994).
Berlin et al., "α4 Integrins Mediate Lymphocyte Attachment and Rolling under Physiologic Flow," *Cell,* 80:413–422 (1995).
Berlin et al., "α4β7 Integrin Mediates Lymphocyte Binding to the Mucosal Vascular Addressin MAdCAM–1," *Cell,* 74:185–195 (1993).
Burkly et al., "Protection Against Adoptive Transfer of Autoimmune Diabetes Mediated Through Very Late Antigen–4 Integrin," *Diabetes,* 43:529–534 (1994).
Capecchi, M.R., "Altering the Genome by Homologous Recombination," *Science,* 244:1288–1292 (1989).
Chan et al., "Adhesion to Vascular Cell Adhesion Molecule 1 and Fibronectin," *J. Biol. Chem.,* 267:8366–8370 (1992).
Chien et al., "The Two–hybrid System: A Method to Identify and Clone Genes for Proteins that Interact with a Protein of Interest," *Proc. Natl. Acad. Sci. (USA),* 88:9578–9582 (1991).
Chisholm et al., "Monoclonal Antibodies to the Integrin α–4 Subunit Inhibit the Murine Contact Hypersensitivity Response," *Eur. J. Immunol.,* 23:682–688 (1993).

Ferguson and Kupper, "Antigen–Independent Processes in Antigen–Specific Immunity," *J. Immunol.,* 150:1172–1182 (1993).
Gumbiner, "Proteins Associated with the Cytoplasmic Surface of Adhesion Molecules," *Neuron* 11:551–564 (1993).
Ingley and Hemmings, "Pleckstrin Homology (PH) Domains in Signal Transduction," *J. Cell. Biochem.,* 56:436–443 (1994).
Kishimoto et al., "Cloning of the β Subunit of the Leukocyte Adhesion Proteins: Homology to an Extracellular Matrix Receptor Defines a Novel Supergene Family," *Cell,* 48:681–690 (1987).
LaFlamme et al., "Regulation of Fibronectin Receptor Distribution," *J. Cell Biol.* 117(2):437–447 (1992).
Lobb and Hemler, "The Pathophysiologic Role of α4 Integrins In Vivo," *J. Clin. Invest.,* 94:1722–1728 (1994).
Macias et al., "Structure of the Pleckstrin Homology Domain from β–spectrin," *Nature,* 369:675 (1994).
Miyamoto et al., "Synergistic Roles for Receptor Occupancy and Aggregation in Integrin Transmembrane Function," *Science* 267:883–835 (1995).
Navone et al., "Cloning and Expression of a Human Kinesin Heavy Chain Gene: Interaction of the COOH–terminal Domain with Cytoplasmic Microtubules in Transfected CV–1 Cells," *J. Biol. Chem.,* 117:1263–1275 (1992).
Pavalko and Otey, "Role of Adhesion Molecule Cytoplasmic Domains in Mediating Interactions with the Cytoskeleton," *Proc. Soc. Exp. Biol. Med.,* 205:282–293 (1994).
Schiller and Kolanus, "A Dominant Negative Effect of the Human Sec7 PH Domain on $\alpha_2$ Itegrin Mediated Binding to ICAM–1," 3rd Adhesion Meeting of the German Immunology Association, Regensburg, Germany, Mar. 14–15 (1995).
Shevell et al., "EMBO30 Is Essential for Normal Cell Division, Cell Expansion, and Cell Adhesion in Arabidopsis and Encodes a Protein that has Similarity to Sec7," *Cell,* 77:1051–1062 (1994).
Springer, "Traffic Signals for Lymphocyte Recirculation and Leukocyte Emigration: The Multistep Paradigm," *Cell,* 76:301–314 (1994).
Tsukada et al., "Binding of βγ Subunits of Heterotrimeric G Proteins to the PH Domain of Bruton Tyrosine Kinase," *Proc. Natl. Acad. Sci. (USA),* 91:11256–11260 (1994).

(List continued on next page.)

*Primary Examiner*—Lila Feisee
*Assistant Examiner*—Claire M. Kaufman
*Attorney, Agent, or Firm*—Marshall, O'Tool, Gerstein, Murray & Borun

[57] ABSTRACT

The present invention provides purified and isolated polynucleotides encoding IRP (integrin regulatory protein) polypeptides which regulate $\beta_2$ and $\beta_7$ integrins and which are contemplated to participate in integrin signaling and/or recycling pathways. Also provided are methods for identifying modulators of IRP activities and methods for identifying other proteins which interact with IRP polypeptides in signaling pathways. Modulators of IRP interactions are contemplated to be useful, for example, in monitoring and treating inflammatory processes involving leukocytes.

6 Claims, 3 Drawing Sheets

OTHER PUBLICATIONS

Van der Vieren et al., "A Novel Leukointegrin, αdβ2, Binds Perferentially to ICAM–3," *Immunity,* 3:683–690 (1995).

Vonderheide et al., "Residues Within a Conserved Amino Acid Motif of Domains 1 and 4 of VCAM–1 are Required for Binding to VLA–4," *J. Cell. Biol.,* 125:125–222 (1994).

Wilson et al., "2.2 Mb of Contagious Nucleotide Sequence from Chromosome III of *C. elegans,*" *Nature,* 368:32–38 (1994).

Yang et al., "Inhibition of Insulitis and Prevention of Diabetes in Nonobese Diabetic Mice by Blocking L–selectin and Very Late Antigen 4 Adhesion Receptors," *Proc. Natl. Acad. Sci. (USA),* 90:10494–10498 (1993).

Yednock et al., "Precention of Experimental Autoimmune Encephalomyelitis by Antibodies Against α4β1 Integrin," *Nature,* 356:63–66 (1992).

Bershadsky, et al. Disruption of the Golgi apparatus by brefeldin A blocks cell polarization and inhibits directed cell migration, *Proc.Natl.Acad.Sci.(USA),* 91:5686–5689 (1994).

Bowman, et al. "Arf proteins: the membrane traffic police?" *TIBS* 20:147–150 (1995).

Bretscher, et al. "Getting Membrane Flow and the Cytoskeleton to Cooperate in Moving Cells," *Cell,* 87:601–606 (1996).

Chan, et al., "Multiple Functional Forms of the Integrin VLA–2 Can be Derived From a Single $\alpha^2$ cDNA Clone: Interconversion of Forms Induced by an anti–$\beta_1$ Antibody," *J. Cell Biol.* 120:537–543 (1993).

Chardin, et al., "A human exchange factor for ARF contains Sec7– and pleckstrin–homology domains," *Nature,* 384:481–484 (1996).

Diamond, et al., "The dynamic regulation of integrin adhesiveness," *Curr.Biol.* 4:506–517 (1994).

D'Souza, et al. "A Regulatory Role for ARF6 in Receptor–Mediated Endocytosis," *Science* 267:1175–1178 (1995).

Fukuda, et al. "Mutation of the Pleckstrin Homology Domain of Bruton's Tyrosine Kinase in Immunodeficiency Impaired Inositol 1,3,4,5–Tetrakisphosphate Binding Capacity," *J.Biol.Chem.* 271:30303–30306 (1996).

Harlan, et al. "Structural Characterization of the Interaction between a Pleckstrin Homology Domain and Phosphatidylinositol 4,5–Bisphosphate," *Biochemistry* 34:9859–9864 (1995).

Harlow and Lane, *Antibodies, A Laboratory Manual,* Cold Spring Harbor Laboratory, Chapter 9, pp. 319–358 (1988).

Kassner, et al. "Interchangeable α Chain Cytoplasmic Domains Play a Positive Role in Control of Cell adhesion Mediated by VLA–4 a $\beta_1$ Integrin," *J.Exp.Med.* 178:649–660 (1993).

Kolanus, et al., "αLβ2 Integrin/LFA–1 Binding to ICAM–1 Induced by Cytohesin–1, a Cytoplasmic Regulatory Molecule," *Cell,* 86:233–242 (1996).

Kuribara, et al., "Synergistic Activation of Rat Brain Phospholipase D by ADP–ribosylation Factor and rhoA p21, and Its Inhibition by *Clostridium botulinum* C3 Exoenzyme," *J.Biol.Chem.* 270:25667–25671 (1995).

Mahadevan, et al. "Structural Studies on the PH Domains of Db1, Sos1, IRA–1 and αARK1 and Their Differential Binding to $G_{\beta\gamma}$ Subunits," *Biochem.* 34:9111–9117 (1995).

Mohanraj, et al., "Expression and Radiolabeling of Recombinant Proteins Containing a Phosphorylation Motif," *Protein Expr. Purif.* 8:175–182 (1996).

Morla, er al., "Superfibronectin is a functionally distinct form of fibronectin," *Nature* ; 376:193–196 (1994).

Peters, et al. "Overexpression of Wild–type and Mutant ARF1 and ARF6: Distinct Perturbations of Nonoverlapping Membrane Compartments," *J.Cell.Biol.* 128:1003–1017 (1995).

Pitcher, et al. "Pleckstrin Homology Domain–mediated Membrane Association and Activation of the β–Adrenergic Receptor Kinase Requires Coordinate Interaction with $G_{\beta\gamma}$ Subunits and Lipid," *J.Biol.Chem.* 270:11707–11710 (1995).

Sambrook, et al. *Molecular Cloning,* Cold Spring Harbor Laboratory Press, Cold Spring Harbor, New York pp. 9.47–9.51, (1989).

Schreiner, et al. "Leukocyte Migration in Different Systems," *Immunol.* 88:89–96 (1990).

Smyth, et al. "Fibrinogen Binding to Purified Platelet Glycoprotein IIb–IIIa (Integrin $\alpha_{IIb}\beta3$) Is Modulated by Lipids," *J.Biol.Chem.* 267:15568–15577 (1992).

Tjoelker, et al. "Plasma Platelet–activating Factor Acetylhydrolase Is a Secreted Phospholipase $A_2$ with a Catalytic Traid," *J.Biol.Chem.* 270:25481–25487 (1995).

Touhara, et al. "Binding of G Protein βγ–Subunits to Pleckstrin Homology Domains," *J.Biol.Chem.* 269:10217–10220, (1994).

Yao, et al. "The pleckstrin homology domain of Bruton tyrosine kinase interacts with protein kinase C," *Proc.Nat'l.Acad.Sci.(USA)* 91:9175–9179 (1994).

Figure 3

| | | | | | |
|---|---|---|---|---|---|
| CELSC7 | M--------- | --------TL | PKVRKRKAQL | VDEIEALKNE | VREVDEELDQ 33 |
| IRP1 | MEDGV-YEPP | DLTPEERMEL | ENIRRRKQEL | LVEIQRLREE | LSEAMSEVEG 49 |
| IRP-2 | MDLCH-PEPA | ELSSGETEEL | QRIKWHRKQL | LEDIQKLKDE | IADVFAQIDC 49 |
| B2-1 | MEEDDSYVPS | DLTAEERQEL | ENIRRRKQEL | LADIQRLKDE | IAEVANEIEN 50 |
| | | | | | |
| CELSC7 | VYYTHPKSK- | EYHKIVVNGR | KKFNQDPWKA | LDWLASRNVV | AKDPQALALW 82 |
| IRP1 | LEANEGSKTL | QRNRKMAMGR | KKFNMDPKKG | IQFLVENELL | QNTPEEIARF 99 |
| IRP-2 | FESAEESRMA | QKEKELCIGR | KKFNMDPAKG | IQYFIEHKLL | SPDVQDIARF 99 |
| B2-1 | LGSTEERKNM | QRNKQVAMGR | KKFNMDPKKG | IQFLIENDLL | KNTCEDIAQF 100 |
| | | | | | |
| CELSC7 | MKAGEGLSKS | AIGEILGDNR | PFALETLDRF | TKEHKLHDVP | IVPALRQYLF 132 |
| IRP1 | LYKGEGLNKT | AIGDYLGERE | ELNLAVLHAF | VDLHEFTDLN | LVQALRQFLW 149 |
| IRP-2 | LYKGEGLNKT | AIGTYLGERD | PINLQVLQAF | VDCHEFANLN | LVQALRQFLW 149 |
| B2-1 | LYKGEGLNKT | AIGDYLGERD | EFNIQVLHAF | VELHEFTDLN | LVQALRQFLW 150 |
| | | | | | |
| CELSC7 | SFRLPGESQK | INRILEKFAE | VYANQNPS-Y | GNADQAHTVA | YSCIMVNTLL 181 |
| IRP1 | SFRLPGEAQK | IDRMMEAFAQ | RYCLCNPGVF | QSTDTCYVLS | FAVIMLNTSL 199 |
| IRP-2 | SFRLPGEAQK | IDRMMEAFAT | RYCLCNPGVF | QSTDTCYVLS | FSIIMLNTSL 199 |
| B2-1 | SFRLPGEAQK | IDRMMEAFAQ | RYCQCNNGVF | QSTDTCYVLS | FAIIMLNTSL 200 |
| | | | | | |
| CELSC7 | HNPNVKDKPS | LEKYIEMNEQ | LLEKGAITIE | QLTEVYESVS | VTQFKIPDEV 231 |
| IRP1 | HNPNVRDKPG | LERFVAMNRG | INEGGDLPEE | LLRNLYDSIR | NEPFKIPED- 248 |
| IRP-2 | HNPNVRDRPP | FERFVSMNRG | INNGSDLPED | QLRNLFDSIK | SEPFSIPED- 248 |
| B2-1 | HNPNVKDKPT | VERFIAMNRG | INDGGDLPEE | LLRNLYESIK | NEPFKIPED- 249 |
| | | | | | |
| CELSC7 | STSGKGTVND | ILLHAEREGW | LFKQSSNPLF | SGALSWKKRW | FVLSENCLYY 281 |
| IRP1 | --DGND-LTH | TFFNPDREGW | LLKLGG-RV- | ---KTWKRRW | FILTDNCLYY 290 |
| IRP-2 | --DGND-LTH | TFFNPDREGW | LLKLGG-RV- | ---KTWKRRW | FILTDNCLYY 290 |
| B2-1 | --DGND-LTH | TFFNPDREGW | LLKLGGGRV- | ---KTWKRRW | FILTDNCLYY 292 |
| | | | | | |
| CELSC7 | FDQMTDKEPK | GIITLANVGI | RKVEAPSRPF | MFEIF-SLSD | GQ-IKACKTE 329 |
| IRP1 | FEYTTDKEPR | GIIPLENLSI | REVDDPRKPN | CFELYIPNNK | GQLIKACKTE 340 |
| IRP-2 | FEFTTDKEPR | GIIPLENLSV | QKVDDPKKPF | CLELYNPSCR | GQKIKACKTD 340 |
| B2-1 | FEYTTDKEPR | GIIPLENLSI | REVEDSKKPN | CFELYIPDNK | DQVIKACKTE 342 |
| | | | | | |
| CELSC7 | QDGRLVEGRH | SIYKICAVND | EDMRSWINAI | SRMMAPQQ-- | HLL-ARPKST 376 |
| IRP1 | ADGRVVEGNH | MVYRISAPTQ | EEKDEWIKSI | QAAVSVDPFY | EMLAARKKRI 390 |
| IRP-2 | GDGRVVEGKH | ESYRISATSA | EERDQWIESI | RASITRVPFY | DLVSTRKKKI 390 |
| B2-1 | ADGRVVEGNH | TVYRISAPTP | EEKEEWIKCI | KAAISRDPFY | EMLAARKKKV 392 |
| | | | | | |
| CELSC7 | H--------377 | | | | |
| IRP1 | SVKKKQEQP399 | | | | |
| IRP-2 | ASKQ-----394 | | | | |
| B2-1 | SSTKRH---398 | | | | |

CYTOPLASMIC MODULATORS OF INTEGRIN REGULATION/SIGNALING

This application is a continuation-in-part application of co-pending U.S. patent application Ser. No. 08/632,247 filed Apr. 15, 1996.

FIELD OF THE INVENTION

The present invention generally relates to proteins involved in integrin signaling pathways. More specifically, the invention relates to a family of proteins, named integrin regulatory proteins (IRPs) herein, which regulate integrin activities and to two members of that protein family designated IRP-1 and IRP-2.

BACKGROUND

The integrins are heterodimeric surface molecules comprised of an $\alpha$ and a $\beta$ subunit in non-covalent association. All integrins are transmembrane proteins with counter-receptor binding activity localized in the extracellular domain. Integrins also possess relatively short cytoplasmic regions which participate in transmembrane signaling events. Integrins are capable of interacting with other cell-bound counter-receptors and components of the extracellular matrix, as well as soluble factors. Binding of extracellular ligands leads to crosslinking and localized clustering of integrins [Miyamoto, et al., *Science*, 267: 833 (1995)] and formation of focal adhesions wherein the clustered integrin cytoplasmic domains associate with cytoskeletal components including, for example, actin filaments [Pavalko and Otey, *Proc. Soc. Exp. Biol. Med.*, 205: 32767 (1994) and Gumbiner, *Neuron*, 11: 551 (1993)]. While most investigations into integrin physiological activity have focused on identifying specific extracellular counter-receptors, less is known about the specific interactions of integrins with cytoplasmic components. Mutation studies, however, have indicated that the cytoplasmic sequences are required for integrin association with focal contacts [LaFlamme, et al., *J. Cell. Biol.*, 117: 437 (1992)].

While numerous integrins have been identified, certain subsets are unique to leukocytes, with each member of the subset having characteristic cell-specific expression and counter-receptor binding properties. Of leukocyte-specific integrins, at least three $\beta_2$ integrins are known, each comprised of a unique $\alpha$ subunit in association with a $\beta_2$ subunit (designated CD18) [Kishimoto, et al., *Cell*, 48: 681–690 (1987)]. For a review of the state of the art with regard to $\beta_2$ integrins, see Springer, *Cell*, 76: 301–314 (1994). CD11a/CD18, also known as $\alpha_L\beta_2$ or LFA-1, is expressed on all leukocytes and has been shown to bind to ICAM-1, ICAM-2, and ICAM-3. CD11b/CD18, also know as $\alpha_M\beta_2$ or Mac-1, is expressed on polymorphonuclear neutrophils, monocytes and eosinophils and has been shown to bind to ICAM-1, complement factor iC3b, factor X, and fibrinogen. CD11c/CD18, also known as $\alpha_X\beta_2$ or p150/95, is expressed on monocytes, polymorphonuclear neutrophils and eosinophils and has been shown to bind to complement factor iC3b and fibrinogen. In addition, a fourth human $\beta_2$ integrin, designated $\alpha_d\beta_2$, has recently been identified [Van der Vieren, et al., *Immunity*, 3: 683–690 (1995)].

The $\beta_7$ integrin subunit, in association with an $\alpha_4$ subunit is expressed predominately on leukocytes. The cell surface heterodimer recognizes a gut homing counterreceptor designated the mucosa addressin cell adhesion molecule (MadCAM) and appears to play a pivotal role in lymphocyte binding to intestinal tissue [Berlin, et al., *Cell* 74: 185–195 (1993)]. $\alpha_4\beta_7$ has also been shown to bind to VCAM [Chan et al., *J. Biol. Chem.* 267: 8366–8370 (1992)]. In a manner similar to action previously associated only with selectin surface molecules, $\alpha_4\beta_7$ has been shown to participate in selectin-independent lymphocyte attachment to inflamed venules under flow conditions [Berlin, et al., *Cell* 80: 413–422 (1995). Animal models using antibodies immunospecific for the $\alpha_4$ subunit have suggested that $\alpha_4\beta_7$, or $\alpha_4$ in associated with the $\beta_1$ integrin subunit, may play a role in numerous disease states, including, for example, experimental allergic encephalomyelitis [Yednock, et al., *Nature* 356: 63–66 (1992); Baron, et al., *J. Exp. Med.* 177: 57–68 (1993)]; contact hypersensitivity [Ferguson and Kupper, *J. Immunol.* 150: 1172–1182 (1993); Chisholm, et al., *Eur. J. Immunol.* 23: 682–688 (1993)]; and non-obese diabetes [Yang, et al., *Proc. Natl. Acad. Sci.* (*USA*) 90: 10494–10498 (1993); Burkly, et al., *Diabetes* 43: 529–534 (1994); Baron, et al., *J. Clin. Invest.* 93: 1700–1708 (1994)].

The integrins have been shown to be one of the major types of proteins involved in trafficking of leukocytes throughout the body. Leukocytes constantly recirculate between lymphoid organs and other tissues by passing from lymph and blood through the endothelial cell layer of the vasculature and penetrating the underlying tissue. One component of inflammatory and autoimmune diseases is the influx of leukocytes to inflammatory sites. Resolution of inflammation at such sites can be accomplished with monoclonal antibodies immunospecific for integrins which block or inhibit leukocyte function. For review, see Lobb and Hemler, *J.Clin.Invest.* 94: 1722–1728 (1994). Modulation of integrin function is one way in which resolution of inflammation may be effected, but little is known about the specific cytoplasmic components of integrin regulation and signaling.

Liu and Pohajdak, *Biochimica et Biophysica Acta*, 1132: 75–58 (1992) describes a human cDNA clone named B2-1 which encodes a protein having domains homologous to the yeast SEC7 protein, squid kinesin, pleckstrin, and dynamin. The article states that since B2-1 is homologous to only a small portion of the yeast SEC7 protein it has not been unequivocally proven that B2-1 is the human homologue of the yeast protein, which is unlikely given dissimilarities outside the SEC7 motif. The article postulates that B2-1 may be involved in the re-orientation of the golgi/secretory granules of NK cells toward target cells during cytolysis. Schiller and Kolanus ["A dominant negative effect of the human Sec7 PH domain on $\beta_2$ integrin mediated binding to ICAM-1," 3rd Adhesion Meeting of the German Immunology Association, Regensburg, Germany, Mar. 14–15, 1995] describe a human protein having similar motifs which interacts with the cytoplasmic domain of $\beta_2$ integrins and report that overexpression of the PH domain of the protein results in a strong dominant negative effect on the activation dependent avidity of $\beta_2$ integrins in Jurkat cells. However, Schiller and Kolanus do not show: (i) the existence of integrin regulatory proteins (IRPs) which preferentially interact with and/or modulate integrins activity, (ii) IRPs which, when co-transfected with integrin-encoding DNA in COS cells, regulate de novo expression of the co-transfected integrin, or (iii) IRPs which modulate attachment and rolling of JY cells under flow conditions Thus there exists a need in the art to identify molecules which bind to and/or modulate the binding and/or signaling activities of the integrins and to develop methods by which these molecules can be identified. The methods, and the molecules thereby identified, will provide practical means for therapeutic intervention in integrin-mediated immune and inflammatory responses.

BRIEF DESCRIPTION OF THE INVENTION

The present invention provides novel human IRPs that are cytoplasmic components of $\beta_2$ and/or $\beta_7$ integrin regulatory and/or signaling pathways.

In one of its aspects, the present invention provides purified and isolated polynucleotides (e.g., DNAs and RNAs, both coding and non-coding strands thereof) encoding IRP-1 and IRP-2. Polynucleotides contemplated by the invention include genomic DNAs, RNAs, cDNAs and wholly or partially chemically synthesized DNAs. Preferred polynucleotides of the invention comprise the IRP-1 DNA sequence set out in SEQ ID NO: 1, the IRP-2 DNA sequence set out in SEQ ID NO: 3, and DNA sequences which hybridize to the noncoding strands thereof under stringent conditions or which would hybridize but for the redundancy of the genetic code. Exemplary stringent hybridization conditions are as follows: hybridization at 42° C. in 5×SSPE, 45% formamide and washing at 65° C. in 0.2×SSC or at 50° C. in 1×SSC. It is understood by those of skill in the art that variation in these conditions occurs based on the length and GC nucleotide base content of the sequences to be hybridized. Formulas standard in the art are appropriate for determining exact hybridization conditions. See Sambrook et al., 9.47–9.51 in *Molecular Cloning*, Cold Spring Harbor Laboratory Press, Cold Spring Harbor, N.Y. (1989).

The DNA sequence information provided by the present invention makes possible the identification and isolation of DNAs encoding related molecules by well-known techniques such as DNA/DNA hybridization as described above and polymerase chain reaction (PCR) cloning. As one series of examples, knowledge of the sequence of cDNAs encoding IRPs makes possible the isolation by DNA/DNA hybridization of genomic DNA sequences encoding the IRPs and expression control regulatory sequences such as promoters, operators and the like. DNA/DNA hybridization procedures carried out with DNA sequences of the invention under stringent conditions are likewise expected to allow the isolation of DNAs encoding allelic variants of the IRPs; non-human species proteins homologous to the IRPs; and other structurally related proteins sharing one or more of the abilities to interact with members or regulators of the $\beta_2$ and/or $\beta_7$ integrin regulation pathway(s) in which IRPs participate. Polynucleotides of the invention when detectably labelled are also useful in hybridization assays to detect the capacity of cells to synthesize IRPs. The DNA sequence information provided by the present invention also makes possible the development, by homologous recombination or "knockout" strategies [see, Capecchi, *Science*, 244: 1288–1292 (1989)], of rodents that fail to express functional IRPs or that express variant IRPs. Such rodents are useful as models for studying the activities of IRPs and IRP modulators in vivo. Polynucleotides of the invention may also be the basis for diagnostic methods useful for identifying a genetic alteration(s) in an IRP locus that underlies a disease state or states. Also made available by the invention are anti-sense polynucleotides relevant to regulating expression of IRPs by those cells which ordinarily express the same.

The invention also provides autonomously replicating recombinant constructions such as plasmid and viral DNA vectors incorporating polynucleotides of the invention, especially vectors in which the polynucleotides are functionally linked to an endogenous or heterologous expression control DNA sequence and a transcription terminator.

According to another aspect of the invention, host cells, especially unicellular host cells such as prokaryotic and eukaryotic cells, are stably transformed or transfected with DNAs of the invention in a manner allowing expression of IRPs therein. Host cells of the invention are conspicuously useful in methods for the large scale production of IRPs wherein the cells are grown in a suitable culture medium and the desired proteins are isolated from the cells or from the medium in which the cells are grown.

IRP polypeptide products having part or all of the amino acid sequence set out in SEQ ID NO: 2 (IRP-1) and SEQ ID NO: 4 (IRP-2) are contemplated. Use of mammalian host cells is expected to provide for such post-translational modifications (e.g., myristoylation, glycosylation, truncation, lapidation and tyrosine, serine or threonine phosphorylation) as may be needed to confer optimal biological activity on recombinant expression products of the invention. Fusion polypeptides are also provided wherein IRP amino acid sequences are expressed contiguously with amino acid sequences derived from other polypeptides. Fusion polypeptides of the invention include those with modified biological, biochemical, and/or immunological properties in comparison to the naturally occurring polypeptide. Multimeric forms of the IRPs are also contemplated. The polypeptide products of the invention may be full length polypeptides, fragments or variants. Variants comprise IRP products wherein one or more of the specified (i.e., naturally encoded) amino acids is deleted or replaced or wherein one or more nonspecified amino acids are added: (1) without loss of the ability to interact with members or regulators of the $\beta_2$ and/or $\beta_7$ signaling pathway or (2) with disablement of the ability to interact with members or regulators of the $\beta_2$ and/or $\beta_7$ signaling pathway. Proteins which interact with IRPs may be identified by various assays.

A first assay contemplated by the invention is a two-hybrid screen. The two-hybrid system was developed in yeast [Chien et al., *Proc. Natl. Acad. Sci.* (*USA*), 88: 9578–9582 (1991)] and is based on functional in vivo reconstitution of a transcription factor which activates a reporter gene. Specifically, a polynucleotide encoding a protein that interacts with IRPs is isolated by: transforming or transfecting appropriate host cells with a DNA construct comprising a reporter gene under the control of a promoter regulated by a transcription factor having a DNA binding domain and an activating domain; expressing in the host cells a first hybrid DNA sequence encoding a first fusion of part or all of an IRP and either the DNA binding domain or the activating domain of the transcription factor; expressing in the host cells a library of second hybrid DNA sequences encoding second fusions of part or all of putative IRP binding proteins and the DNA binding domain or activating domain of the transcription factor which is not incorporated in the first fusion; detecting binding of an IRP interacting protein to IRPs in a particular host cell by detecting the production of reporter gene product in the host cell; and isolating second hybrid DNA sequences encoding the interacting protein from the particular host cell. Presently preferred for use in the assay are a GAL4 upstream activation sequence to drive expression of the lacZ reporter gene, a transcription factor comprising the GAL4 DNA binding domain and the GAL4 transactivation domain, and yeast host cells.

Other assays for identifying proteins that interact with IRPs may involve immobilizing IRPs or a test protein, detectably labelling the non-immobilized binding partner, incubating the binding partners together and determining the amount of label bound. Bound label indicates that the test protein interacts with IRPs.

Another type of assay for identifying IRP interacting proteins involves immobilizing IRPs or fragments thereof on a solid support coated (or impregnated with) a fluorescent agent, labelling a test protein with a compound capable of exciting the fluorescent agent, contacting the immobilized IRPs with the labelled test protein, detecting light emission by the fluorescent agent, and identifying interacting proteins as test proteins which result in the emission of light by the fluorescent agent. Alternatively, the putative interacting protein may be immobilized and IRPs may be labelled in the assay.

Also comprehended by the present invention are antibody products and other binding proteins (such as those identified in the assays above) which are specific for the IRPs of the invention. Antibody products of the invention include monoclonal, polyclonal, anti-idiotypic, and recombinant (i.e., humanized, chimeric, etc.) antibodies and fragments thereof. Cell lines (e.g., hybridoma cell lines) producing antibody products of the invention are contemplated. Binding proteins can be developed using isolated natural or recombinant IRP polypeptide products. The binding proteins are useful, in turn, for purifying recombinant and naturally occurring IRP polypeptide products and identifying cells producing such products. Assays for the detection and quantification of proteins in cells and in fluids may involve a single antibody substance or multiple antibody substances in a "sandwich" assay format. The binding proteins are also manifestly useful in modulating (i.e., blocking, inhibiting, or stimulating) IRP interactions with $\beta_2$ and/or $\beta_7$ integrin signaling pathway components.

Specifically illustrating the monoclonal antibodies of the present invention are monoclonal antibodies produced by hybridoma cell lines 200A, 200B and 233G. These cell lines were deposited with the American Type Culture Collection (ATCC), 12301 Parklawn Drive, Rockville, Md. 20852 on Apr. 2, 1997. The deposit number for 200A is HB-12331, 200B is HB-12332, and 233G is HB-12333.

Assays for identifying compounds that modulate interaction of IRPs with other proteins or lipids may involve: transforming or transfecting appropriate host cells with a DNA construct comprising a reporter gene under the control of a promoter regulated by a transcription factor having a DNA-binding domain and an activating domain; expressing in the host cells a first hybrid DNA sequence encoding a first fusion of part or all of an IRP and the DNA binding domain or the activating domain of the transcription factor; expressing in the host cells a second hybrid DNA sequence encoding part or all of a protein that interacts with IRPs and the DNA binding domain or activating domain of the transcription factor which is not incorporated in the first fusion; evaluating the effect of a test compound on the interaction between the IRP and the interacting protein by detecting binding of the interacting protein to IRPs in a particular host cell by measuring the production of reporter gene product in the host cell in the presence or absence of the test compound; and identifying modulating compounds as those test compounds altering production of the reported gene product in comparison to production of the reporter gene product in the absence of the modulating compound. Presently preferred for use in the assay are a GAL4 upstream activation sequence to drive expression of the reporter gene, the lacZ reporter gene, a transcription factor comprising the GAL4 DNA binding domain and the GAL4 transactivation domain, and yeast host cells.

Another type of assay for identifying compounds that modulate the interaction between IRPs and an interacting protein or lipid involves immobilizing IRPs or a natural IRP interacting protein, detectably labelling the nonimmobilized binding partner, incubating the binding partners together and determining the effect of a test compound on the amount of label bound wherein a reduction in the label bound in the presence of the test compound compared to the amount of label bound in the absence of the test compound indicates that the test agent is an inhibitor of IRP interaction with the protein. Conversely, an increase in the label bound in the presence of the test compound compared to the amount of label bound in the absence of the compound indicates that the putative modulator is an activator of IRP interaction with the protein.

Yet another method contemplated by the invention for identifying compounds that modulate the binding between IRPs and an interacting protein or lipid involves immobilizing IRPs or fragments thereof on a solid support coated (or impregnated with) a fluorescent agent, labelling the interacting protein with a compound capable of exciting the fluorescent agent, contacting the immobilized IRPs with the labelled interacting protein in the presence and absence of a test compound, detecting light emission by the fluorescent agent, and identifying modulating compounds as those test compounds that affect the emission of light by the fluorescent agent in comparison to the emission of light by the fluorescent agent in the absence of the test compound. Alternatively, the IRP interacting protein may be immobilized and IRPs may be labelled in the assay.

Modulators of IRPs may affect ARF, PI, $\beta_1$, $\beta_2$, $\beta_3$ and/or $\beta_7$ integrin regulation and signaling activities, IRP localization in the cell, and/or IRP interaction with members of the ARF, PI, $\beta_1$, $\beta_2$, $\beta_3$ and/or $\beta_7$ integrin signaling pathways. Combinatorial libraries, peptide and peptide mimetics, defined chemical entities, oligonucleotides, and natural product libraries may be screened for activity as modulators in assays such as those described above. Selective modulators may include, for example, polypeptides or peptides which specifically bind to IRPs or IRP nucleic acid, oligonucleotides which specifically bind to IRPs or IRP nucleic acid, and/or other non-peptide compounds (e.g., isolated or synthetic organic molecules) which specifically react with IRPs or IRP nucleic acid. Mutant forms of IRPs which affect the binding activity or cellular localization of wild-type IRPs are also contemplated by the invention. Modulators of ARF, PI, $\beta_1$, $\beta_2$, $\beta_3$ or $\beta_7$/IRP interaction identified by the methods of the invention are utilized in vitro or in vivo to affect inflammatory processes involving leukocytes. In addition, modulating compounds which bind to ARF, PI, $\beta_1$, $\beta_2$, $\beta_3$ and/or $\beta_7$ integrins or IRPs are useful in monitoring the levels of ARF, PI, $\beta_1$, $\beta_2$, $\beta_3$ and/or $\beta_7$ in biological samples including body fluids or biopsies tissue.

IRP modulators may be formulated in compositions comprising pharmaceutically acceptable carriers. Dosage amounts indicated would be sufficient to result in modulation of IRP/$\beta_1$, $\beta_2$, $\beta_3$ or $\beta_7$ integrin signaling or regulation in vivo.

Numerous other aspects and advantages of the present invention will be apparent upon consideration of the following detailed description.

BRIEF DESCRIPTION OF THE DRAWINGS

FIG. 3 shows an alignment of the amino acid sequences of IRP-1 (SEQ ID NO: 2), IRP-2 (SEQ ID NO: 4), B2-1 (SEQ ID NO: 32) and a C. elegans homolog of B2-1 (SEQ ID NO: 31).

DETAILED DESCRIPTION OF THE INVENTION

Figure 1:
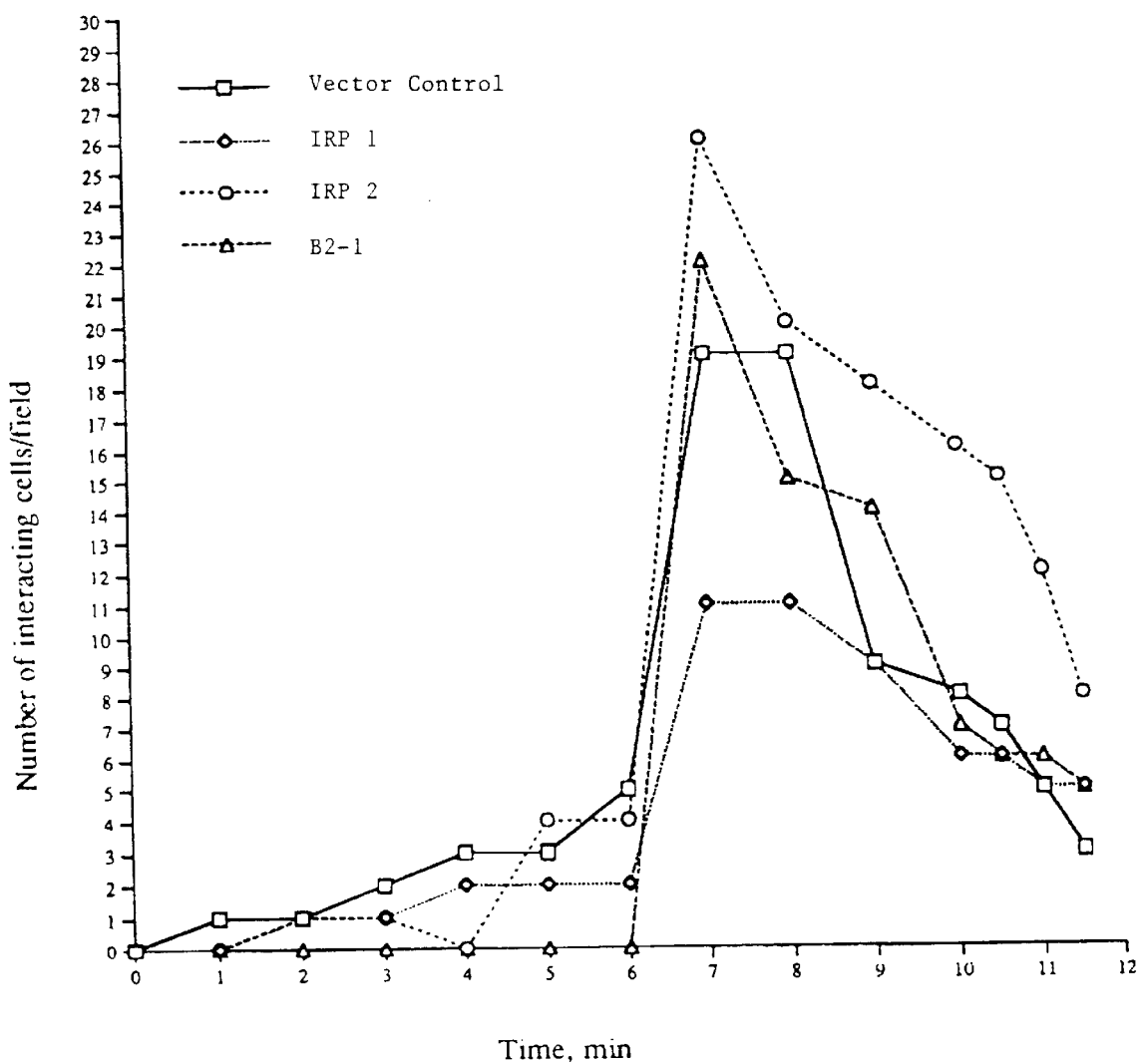
FIG. 1 presents a graph showing the ability of JY cells, expressing the indicated polypeptides, to bind to VCAM-1.

The present invention is illustrated by the following examples wherein Example 1 describes the isolation of cDNAs encoding IRP-1 and IRP-2 and Example 2 provides an analysis of the domain structure of the IRP-1 and IRP-2 proteins encoded by the cDNAs. Recombinant expression constructs containing the full length IRP cDNAs and cDNAs encoding IRP domains and IRP mutations are described in Example 3. Presented in Example 4 are the results of assays in which the effects of recombinant expression of the IRPs on host cell adhesion are analyzed, including the role of IRPs on cell adhesion to ICAM-1 and VCAM-1, the role of IRPs in cell surface expression of integrins, and subcellular localization of IRPs. Example 5 describes the preparation of a stably transformed JY cell line (JY-8) that stably expresses IL-8 receptor and its use in determining the role of IRPs on IL-8-dependent and PMA-stimulated cell adhesion to ICAM-1 and VCAM-1. Example 5 also describes the preparation of expression vectors encoding green fluorescent protein (GFP) IRP fusion proteins. Example 6 describes adhesion of JY cells transfected with IRPs under flow conditions. The preparation and characterization of monoclonal antibodies to IRPs is described in Example 7. The role of IRPs in chemotaxis is characterized in Example 8. Example 9 describes experiments showing the distribution of IRPs in various human tissues. Assays to identify proteins which interact with IRPs are described in Example 10 while assays to identify modulators of IRP interactions are described in Examples 11 and 12.

EXAMPLE 1

Two human IRP cDNA clones were isolated using the polymerase chain reaction (PCR) and DNA/DNA hybridization.

A BLAST search identified various partial cDNAs exhibiting similarity to the B2-1 protein. Consensus sequence oligonucleotide primers corresponding to the 5' and 3' ends of regions representing pleckstrin homology domains were designed based on the ESTs H02055, R82669, R43994, H39073, R45477, T07442, and T32215. The sequences of the primers designed to the 5' end (TS3.5) and 3' end (TS3.3) were:

TS3.5 ATATACGCGTACCTTCTTCAACCCGGACC (SEQ ID NO: 5)
TS3.3 ATATGTCGACTCAGGGCTGCTCCTGCTTC (SEQ ID NO: 6)

The primers were used in a 100 μl PCR reaction using human spleen cDNA as template 2 mg of plasmid cDNA in pcDNA-1 Amp (Invitrogen, San Diego, Calif.)]. Samples held at 94° C. for five minutes and then run through 30 cycles of: 94° C., one minute; 50° C., one minute; 72° C., two minutes. The resulting PCR product of about 450 bp was digested with MluI and SalI. The purified digested fragment was cloned into the vector pCl-neo (Promega, Madison, Wis.) which had sequences encoding a hemagglutinin tag immediately 5' to the site of insertion of the digested PCR fragment. The sequence of the resulting insert was verified and the vector was named 5'HA TS53/pCl #3.

The MluI/SalI digested PCR product was labeled and used to probe a human spleen cDNA library size selected for greater than 3 kb inserts. The spleen library was prepared by cloning an oligo-dT primed cDNA library into pcDNA-1 Amp and size selecting vector/insert DNA greater than about 7.8 kb. The library vectors were transformed into XL1 Blue Ultracompetent Cells (Stratagene, La Jolla, Calif.) and plated on 15 master 150 mm² plates with Hybond N⁺ filters at a density of about 20,000 colonies/plate. Two replicas made from each master were used in hybridizations. The digested PCR fragment (400 ng) was labeled with 120 μCi $^{32}$P dCTP and dTTP using the Boehringer Mannheim Random Primed Labeling Kit according to the manufacturers' suggested protocol. Unincorporated nucleotides were removed via Centri-sep columns (Princeton Separations, Adelphia, N.J.). The probe was hybridized in a solution containing (5xSSPE, 45% formamide, 5xDenhardts, 1% SDS) at 42° C. overnight. Filters were washed to a final stringency of 0.2xSSC at 65° C. and exposed to film. Positives on duplicate filters were picked, diluted, and replated on Hybond N⁺ filters on LBM plates. Two duplicates were made from each of these masters which were rehybridized with the hybridization solution saved from the primary screen. Secondary positives were picked, grown, and the plasmids were isolated and both ends of the insert were sequenced.

One clone identified contained a full length gene which was named clone S3 and the protein encoded thereby is designated IRP-1 herein. The nucleotide and deduced amino acid sequences of the clone are set out in SEQ ID NOs: 1 and 2. The clone has an optimal Kozak consensus sequence surrounding its initiating methionine and a stop codon in frame 5' of the methionine. The clone is approximately 1.6 kb in length and has an open reading frame of 399 amino acids. Clone S3 is most similar to EST R82724, showing homology of greater than 93% over 469 nucleotides.

Another clone was recovered which is approximately 3.4 kb in length. This clone, named S12 which encodes a protein designated herein as IRP-2, exhibits homology to IRP-1 but is clearly a novel gene. The IRP-2 clone was not full length since alignment of its 5' end with IRP-1 sequence placed it approximately fifty amino acids into the coding region of the IRP-1 clone.

In order to obtain a full length IRP-2 clone, the same spleen cDNA library (described above) was rescreened using two IRP-2 probes as follows. The truncated IRP-2 clone was digested separately with XbaI and XhoI. A 2 kb XbaI fragment and 1 kb XhoI fragment were then labeled as described above using the Boehringer Mannheim Random Primed Labeling Kit. Unincorporated nucleotides were removed using a Centri-sep column and the probe was added to the filters in hybridization solution as described above and hybridized overnight at 42° C. The filters were washed to a final stringency of 1xSSC/0.1% SDS at 50° C. Primary positives were picked, diluted and repeated on Hybond N⁺ filters on LBM plates. Two duplicate filters were made from each of these masters which were rehybridized with the saved hybridization buffer from above. Positives on duplicate filters were picked, grown, and their plasmids were isolated and inserts sequenced. Two clones, S12-41 and S12-47, extended the IRP-2 coding region about 50 amino acids in the 5' direction. There is a methionine at the 5' end of the clones which maintains about the same amino acid organization seen in the IRP-1 clone and a good match to the Kozak consensus sequence surrounding the methionine. The S12-47 clone was fully sequenced and the IRP-2 DNA and deduced amino acid sequences are set out in SEQ ID NOs: 3 and 4.

EXAMPLE 2

Three common domains or motifs were identified by comparison of the IRP-1, IRP-2, B2-1 (Liu et al., supra) genes and deduced amino acid sequences: an amino terminal kinesin/myosin domain, a SEC7 domain, and a carboxyl terminal pleckstrin homology (PH) domain. Kinesin and myosin are transport proteins associated with microtubules [Navone, et al., *J. Biol. Chem.* 117: 1263–1275 (1992)]. The yeast protein SEC7, described in Altschul et al., *J. Mol. Biol.*, 215: 403–410 (1990), is a 2008 amino acid protein which appears to regulate glycoprotein secretion from the Golgi apparatus. While a more precise function of SEC7 in yeast has not been determined, a SEC7 gene mutation in Arabidopsis results in modulation of development-related cell division and cell adhesion [Shevell, et al., *Cell,* 77: 1051–1062 (1994)]. PH domains are found in a large number of proteins involved in signal transduction. In some proteins the domain confers the ability to bind to G protein βγ subunits, inositol triphosphate ($IP_3$), or phosphatidyl inositol diphosphate ($PIP_2$). See Ingley and Hemmings, *J. Cell. Biochem.*, 56: 436–443 (1994). In the amino acid sequences of IRP-1 and IRP-2, the kinesin/myosin domain extends from approximately residue 9 to approximately residue 60, the SEC7 domain from approximately residue 71 to approximately residue 245, and the PH domain from approximately residue 260 to the carboxy terminus. In B2-1, the kinesin/myosin, SEC7, and PH domains are approximately defined from approximately residue 10 to approximately residue 61, approximately residue 72 to residue 245, and approximately residue 246 to the carboxy terminus, respectively. The amino acid identity between the various domains in IRP and B2-1 is shown in Table 1 below.

TABLE 1

| | Kinesin/Myosin | B2-1 SEC7 domain | PH domain |
|---|---|---|---|
| IRP-1 | 59% | 88% | 90% |
| IRP-2 | 34% | 79% | 72% |

Based on the conservation of the kinesin/myosin, SEC7, and PH domains in the three proteins, the IRP-1 and IRP-2 proteins appear to represent members of a family of human proteins related to B2-1. FIG. 3 shows an alignment of the IRP-1, IRP-2, and B2-1 clones with an apparent *C. elegans* homolog [Wilson et al., *Nature,* 368: 32–38 (1994)]. While the percent identity of the *C. elegans* protein to the other three human proteins is not very high, it is clear that overall domain structure is conserved among the four proteins.

Most residues conserved between the three human proteins and the *C. elegans* protein are also conserved in an Arabidopsis protein [Shevell et al., supra] which contains homologous SEC7 region and are additionally conserved in the yeast SEC7 protein. This suggests the importance of these residues in the function of the SEC7 domain. In fact, Shevell et al., supra, reported that in the Arabidopsis clone (EMB30), a mutation changing one of these residues (corresponding to position 157 in the alignment in FIG. 3) affected cell division, elongation, and adhesion.

Conserved residues in IRP PH domains may also be functionally important. Tsukada et al., *Proc. Natl. Acad. Sci. (USA),* 91: 11256–11260 (1994) reports that the mutation of an arginine (corresponding to position 289 in FIG. 3) conserved in many PH domains to a cysteine, when present in the PH domain of the btk tyrosine kinase in mice, led to a X-linked immuno-deficient phenotype despite the enzyme maintaining full btk kinase activity. The authors speculated since this residue is predicted to be on the surface of the molecule, it is unlikely this substitution has a structural effect, but more likely disrupt a specific interaction with another protein. This residue is also conserved among the human IRP proteins and the *C. elegans* protein.

Finally, all three human proteins as well as the *C. elegans* protein have an additional sixteen to eighteen residues between subdomains 5 and 6 in their PH domains when compared to other PH domains. If evaluated in view of the proposed three-dimensional structure of the PH domain described in Macias et al., *Nature,* 369: 675 (1994), this domain would create a loop extending from the core of the domain and might therefore be important for an interaction with another protein or proteins. These sixteen to eighteen residues exhibit 73% identity between the four proteins.

EXAMPLE 3

In order to study the role of the IRP proteins in integrin function, the IRP-1, IRP-2, and B2-1 proteins or PH domains thereof were expressed in COS and JY cells along with the $β_2$ integrin subunits CD11a and CD18. IRP and B2-1 expression vectors were constructed as follows. Expression of the proteins using the vectors is described in Example 4.

Complementary DNA encoding the human B2-1 protein was cloned by PCR amplification of a size-selected 2.5–4 kb Ramos library. Primers to the 5' and 3' ends of the coding region were designed based on the previously published sequence (Liu et al., supra). Primer pairs were designed to facilitate insertion of amplified sequences into appropriate vectors. The B2-1 cDNA was first amplified and cloned into the vector pET 15b (Novagen, Madison, Wis.) using the 5' Sc7.Nde and 3' Sc7.Xho primers:

Sc7.Nde ATATCATATGGAGGAGGACGACAGCTAC (SEQ ID NO: 7)

Sc7.Xho ATATCTCGAGTCAGTGTCGCTTCGTGGAG (SEQ ID NO: 8)

The primers were used in a 100 μl PCR reaction. Samples were held at 94° C. for 5 minutes and then run through 30 cycles of the sequence: 94° C., 30 seconds; 55° C., 30 seconds; and 72° C., 1 minute. The resulting PCR product was gel purified, digested with NdeI and XhoI and cloned into pET 15b. Clones were sequenced and clones Sc7/pET #5 and Sc7/pET #6 contained an insert having a sequence identical to the published B2-1 sequence.

An HA tag was added to the 5' end of the B2-1 cDNA by PCR and then the tagged gene was cloned into pCl-neo. The 3' Sc7.Xho primer described above was utilized with the 5' Sc7.HAS primer:

Sc7.HAS ATATGCTAGCCACC ATGGGGTACCCATACGATGTTCCTGACTATGCG-ACGCGTATGGAGGAGGACGACAGC (SEQ ID NO: 9)

The underlined nucleotides in the primer encode the HA tag. The primers were used in a 100 μl PCR reaction with Sc7/PET #6 DNA as template under the following conditions. Samples held at 94° for 5 minutes and then run through 30 cycles of: 94° C., 1 minute; 55° C., 1 minute; and 72° C. 2 minutes. The resulting PCR product was gel purified, digested with NdeI and XhoI and cloned into a pCl-neo vector digested with NdeI/XhoI. The resulting clone was named 5' HASc7/pCl #29. Its insert encoded a HA fusion protein named 5'HA B2-1 herein.

An HA tag was added to the 3' end of the B2-1 cDNA by PCR and the tagged cDNA was then cloned into pCl-neo. The primers used were Sc7.HA3 and T7:

Sc7.HA3 ATATGTCGACTCA CGCATAGTACAGGAACATCGTATGGGTACAT-ACGCGTGTGTCGCTTCGTGGAGGA (SEQ ID NO: 10)

T7 TAATACGACTCACTATAGGG (SEQ ID NO: 11)

These primers were used in a 100 μl PCR reaction with SEC7/pCl #9 DNA as template under the following conditions. Samples were held at 94° C. for 5 minutes and then run through 30 cycles of sequence: 94° C. for 1 minute; 55° C. for 1 minute; and 72° for 2 minutes. The resulting PCR product was gel purified, digested with XhoI and SalI and ligated into pCl-neo previously cut with XhoI and SalI. The construct was named 3'HA B2-1/pCl #29 and its encoded protein was named 3'HA B2-1.

The B2-1 PH domain was subcloned by PCR using 5' Tsc7.S and 3' Sc7.Xba primers:
Tsc7.5 ATATACGCGTACTTTCTTCAATCCAGACCG (SEQ ID NO: 12)
Sc7.Xba ATATTCTAGATCAGTGTCGCTTCGTGGAG (SEQ ID NO: 13)

The primers were used in a 100λ PCR reaction with SEC7/pET #5 DNA as template under the following conditions. Samples held at 94° C. for 5 minutes followed by 30 cycles of: 94° C., one minute; 50° C., one minute; and 72° C., two minutes. The resulting PCR product was gel purified, digested with Mlu1 and Xba1 and cloned into 5'HA pCl-neo previously cut with MluI/XbaI (prepared by cutting 5'HA B2-1/pCl #29 clone with MluI and XbaI). The insert of the resulting clone encoded an HA fusion protein named 5'HA B2-1 PH herein.

The IRP-1 cDNA was subcloned into the 5'HA pCl vector by first using PCR to add an Mlu site to the 5' end of the cDNA and a Sal1 site to the 3' end of the clone. The primers used were:
S3.5' HA ATATACGCGTATGGAGGACGGCGTCTATG (SEQ ID NO: 14)
TS3.3 (SEQ ID NO: 6)

The primers were used in a 100 μl PCR reaction with S3.3 DNA as template under the following conditions. Samples were held at 94° C. for 5 minutes followed by 30 cycles of: 94° C., 45 seconds, 50°, 45 seconds; and 72°, 1 minute. The PCR product was gel purified, digested with Mlu and Sal1 and ligated into 5'HA pCl previously digested with Mlu and Sal1. The resulting clone was named 5'HA IRP-1/pCl #15 and the protein encoded thereby was named 5'HA IRP-1.

Clone 5'HA TS3/pc1 #3 (Example 1) was used to express the IRP-1 PH domain.

IRP-2 was first cloned into pCl-neo using PCR without an HA tag. The primers used were:
S12/SR1 ATATGAATTCCACCATGGACCTGTGC-CACCCAG (SEQ ID NO: 15)
TS12.3 ATATGTCGACTCACTGCTTGCTGGCAATC (SEQ ID NO: 16)

These primers were used in a 100 μl PCR for 30 cycles with clone 5'HAS12/pCl as template under the following conditions: 94° C., one minute; 50° C., one minute; and 72° C., one minute. The resulting amplification product was purified, digested with EcoRI and SalI, and ligated into a pCl-neo vector previously digested with the same two enzymes. The resulting clone #11 was fully sequenced and found to be identical to the original clone.

In addition, IRP-2 and the IRP-2 PH domain were separately cloned into pCl-neo with a 5'HA tag using PCR and the primers TS12.5 (SEQ ID NO: 17), TS12.3 (SEQ ID NO: 18) and S12.5 (SEQ ID NO: 19).
TS12.5 ATATACGCGTACCTTCTTCAATCCAGAC (SEQ ID NO: 17)
ST12.3 ATATGTCGACTCACTGCTTGCTGGCAATC (SEQ D NO: 18)
S12.5 ATATACGCGTATGGACCTGTGCCACCCAG (SEQ ID NO: 19)

Template DNA for the amplification reactions was clone S12. Samples were held at 94° C. for four minutes, and followed by t30 cycles of: 94° C. for one minute; 52° C. for two minutes, and 72° C. for two minutes. Each of the two resulting amplification products was digested with MluI and SalI, purified and separately ligated into a pCl-neo HA vector previously digested with MluI and SalI. Clones pCl-neo HA IRP-2 #8 and pCl-neo IRP-2 PH #5 were sequenced and found to be identical to corresponding sequences in the template clone.

EXAMPLE 4

The effects of overexpressing IRPs on $\beta_2$ dependent cell adhesion (measured by binding of transfected COS or JY cells to ICAM-1) and on $\beta_7$ dependent cell adhesion (measured by binding of transfected JY cells to VCAM-1) were determined.

COS cells were co-transfected with vectors encoding CD11a/CD18 and vectors (Example 3) having inserts encoding one of 5'HA B2-1, 3'HA B2-1, 5'HA B2-1 PH, 5'HA IRP-1, 5'HA IRP-1 PH, 5'HA IRP-2, 5'HA IRP-2 PH, or a pCl-neo vector control. COS cells were split $1.2 \times 10^6$ cells per 10 cm$^2$ plate 24 hours prior to transfection. The next day a transfection mix was prepared for each plate containing 5 ml DMEM, 2 μl of chloroquine (0.25 M), 30 μl of DEAE Dextran (50 mg/ml in CMF-PBS) and 10 μg of each vector DNA being transfected into the cells. The growth media was removed from approximately 80% confluent plates of COS cells, and the transfection mix was added. The plates were incubated for 2.5 hours at 37° C. The transfection mix was removed by aspiration and a 10% solution of DMSO in DMEM was added for one minute (room temperature). After one minute, the DMSO was removed by aspiration and 10 ml of complete media was added.

Expression of LFA-1 and IRPs by the transfected COS cells was confirmed using various antibodies. All transfectants stained positive for CD18. IRP transfectants all stained positive for the HA epitope using an HA tag specific monoclonal antibody 150B OR 12CA5.

The transfected cells were tested for their ability to bind ICAM-1 at 48 and 72 hours after transfection. To prepare cells for an adhesion assay, the growth media was removed by aspiration, 5 ml versene was added to the plate for three minutes and then the cells were recovered. Five ml of complete DMEM was added and then the cell suspension was spun down at 1,000 rpm for five minutes. The cells were resuspended in complete DMEM and counted. Adhesion assays with the variously transfected cells were carried out as described below.

Individual 96 well plates (Corning, Cambridge, Mass.) were initially coated with either ICAM-1/Fc or VCAM-1/Fc in carbonate buffer, pH 9.6, at 50 μl/well of 5 μg/ml protein and incubated overnight at 4° C. The plates were washed two times with 150 μl/well PBS and blocked with 150 μl/well 1% BSA in PBS for one hour at room temperature. Following blocker, 100 μl adhesion buffer (RPMI media with 10% fetal bovine serum) was added to each well along with 100 μl transfected JY cells suspended in adhesion buffer at room temperature. The transfected cells were prepared as follows.

The day prior to assay, transfected cells were split to a density of $3 \times 10^5$ cells/ml in RPMI media supplemented with penicillin/streptomycin, L-glutamine, sodium pyruvate and 10% fetal calf serum. Cells were allowed to double, generally after 24 hour incubation. After doubling, cells were harvested and resuspended at a density of $1 \times 10^6$ cells/ml in adhesion buffer. Approximately $1 \times 10^5$ cells in 100 μl were added to each well, and the plates incubated for 30 minutes at room temperature while covered.

Following incubation, cells were fixed by addition of 50 μl/well 14% glutaraldehyde in CMF-PBS and incubation for 30 minutes at room temperature. After incubation, the wells were washed three times with deionized water. Following the last wash, the water was removed by aspiration, 50 µl stain containing 0.125% Crystal Violet (prepared as a stock solution of 1% in 10% ethanol and 90% deionized water, diluted to 0.125% with deionized water and filtered through a 0.22 micron filter), and the plates incubated for two minutes. After incubation, the plates were washed three times with deionized water as described above, and 200 µl/well ethanol solution (two parts 95% ethanol and one part deionized water) was added. After one hour incubation, the plates were read on an ELISA reader at a wavelength between 570 and 590 nm.

At 48 hours post-transection, B2-1 PH domain transfectants demonstrated a moderate decrease in LFA-1 dependent adhesion relative to vector control transfectants. There was a marked decrease in binding of IRP-2 PH domain transfectants whereas full length IRP clones showed no significant change in adhesion relative to the pCl-neo vector control. At 72 hours post-transection, four transfectants (3'HA B2-1, 5'HA B2-1, B2-1 PH, IRP-1 PH) demonstrated a 50% decrease in ICAM-1 adhesion compared with the vector control.

JY cells, which express endogenous $\alpha_4\beta_7$ and LFA-1, were individually transfected with vectors encoding either IRP-1, IRP-2, B2-1, IRP-1 PH, IRP-2 PH, or B2-1 PH. Cells were transfected by electroporation using a standard protocol. Briefly, for each transformation $10^7$ JY cells were spun down and kept on ice. The cells were rinsed with DPBS and respun. The cells were then resuspended in 0.5 ml DPBS and transferred to an electroporation cuvette. Thirty µg of DNA (1 mg/ml in DPBS) was added to each transformation mix. The transformation mix was mixed gently and incubated on ice for 10 minutes. The cells were electroporated using a BioRad Gene Pulser using the following parameters: capacitance extender on, voltage at 250 V, and capacitance at 960 µf. After electroporation, the transfection mix was incubated on ice for ten minutes. The cells were then placed in a T25 flask with 5 ml complete RPMI media. Three days post-transection, hygromycin was added to the media at a concentration of 0.5 mg/ml. Adhesion assays were performed 14 days post-transection.

JY cells transfected with IRPs also demonstrated a decrease in LFA-1 dependent adhesion to ICAM-1 and $\alpha_4\beta_7$ adhesion to VCAM-1. LFA-1 and $\alpha_4$ levels were not significantly different between transfectants, and therefore do not explain decreases in adhesion.

IRPs thus appear to demonstrate some specificity for modulating $\beta_2$ or $\beta_7$ integrin dependent adhesion. IRP-1 expressed in JY cells appears to preferentially decrease $\beta_2$ dependent adhesion whereas IRP-2 appeared to down regulate $\beta_7$ dependent adhesion. B2-1 transfectants demonstrate both decreased $\beta_2$ and $\beta_7$ adhesion. The expression of truncates consisting of the PH domain of IRP-1, IRP-2, or B2-1 appeared to generally decrease both $\beta_2$ and $\beta_7$ dependent adhesion. See Table 2 below where a "+" represents an increase in adhesion, an "−" indicates a decrease in adhesion, and "NS" represents no significant change in adhesion.

TABLE 2

| | Host Cell | | |
| --- | --- | --- | --- |
| | JY | | COS |
| Expressed Protein | $\beta_2$ | $\beta_7$ | $\beta_2$ |
| 5'HA IRP-1 | — | NS/+ | — |
| 5'HA IRP-2 | NS | — | NS |
| 5'HA B2-1 | — | Ns/+ | — |
| 5'HA IRP-1 PH | — | NS/− | — |
| 5'HA IRP-2 PH | — | NS/− | NS |

These results would be consistent with the amino terminal portion of IRPs interacting directly or indirectly with $\beta_2$ or $\beta_7$ integrins with differing affinities resulting in preferential regulation of one or the other type of integrin. The functions and interaction of the PH domains, in contrast, may be a common signaling element in pathways regulating different integrins. This element may be heterotrimeric GTP binding proteins (e.g. $G_{\alpha\beta\gamma}$) $PIP_n$, protein kinase C (PKC) or some as yet unidentified ligand of PH domains. An antagonist that disrupts IRP PH domain binding to this common signaling element would be predicted to broadly regulate adhesion of $\beta_2$, $\beta_7$, and perhaps other integrins such as $\beta_1$ and $\beta_3$ integrins. In contrast, an antagonist that disrupts the amino terminal interaction of IRPs with integrin may be predicted to regulate integrin dependent adhesion in a more specific manner.

Leukocytes and leukocyte cell lines that are not maximally activated for integrin dependent cell adhesion can be activated by PKC agonists such as the phorbol ester PMA. The mechanism by which PKC activity induces cell adhesion is not well defined; PKC may have some effect on affinity or avidity upregulation, as well as cytoskeletal reorganization required for cell spreading. However, the effect of PKC activation on IRP down regulation of integrin dependent adhesion may indicate if PKC functions downstream or upstream of IRP. Phorbol stimulation of JY transfectants described above often does not restore LFA-1 or $\alpha_4\beta_7$ dependent adhesion to vector control levels. Thus either the regulatory PKC substrate may be upstream in the pathway regulated by IRPs, or PKC regulates a different pathway or aspect of integrin dependent adhesion. Alternatively, IRPs may regulate multiple aspects of integrin dependent adhesion and PKC stimulation may only affect one of these. IRPs may regulate integrin dependent adhesion by affecting integrin affinity, avidity (clustering) (Example 4), or membrane recycling. A role in integrin recycling is suggested by decreased LFA-1 levels on COS cells expressing IRPs but not in COS cells expressing IRP PH domains.

In order to determine if IRPs exert an effect on cell surface expression of integrins, COS cells were co-transfected with DNAs encoding either full length IRP-1, IRP-2, or B2-1 (or with a control DNA vector pCl-neo or DNA encoding 14-3-3θ) along with DNA encoding either $\alpha_L\beta_2$, $\alpha_4\beta_7$, or ICAM-2. Cells were stained for surface expression (fluorescence intensity and percent positive cells) using monoclonal antibodies ICA4.1 (immunospecific for $\alpha_4$), TS1/22 (immunospecific for $\alpha_L$), 3S3 (immunospecific for $\beta_1$), or 92C12F (immunospecific for ICAM-2). $\beta_1$ is endogenously expressed in COS cells and no $\beta_1$ encoding DNA was required for transfection.

The results, presented in Table 3 below, suggest that IRP-1 decreases cell surface expression of $\alpha_L\beta_2$ integrin, possibly through down regulation of de novo biosynthesis or a recycling process which removes and replaces the integrin on the cell surface.

TABLE 3

IRP Effect on Cell Surface Integrin Expression

|  | $\alpha_L$ | $\beta_1$ | $\alpha_4$ | $\beta_1$ | ICAM-2 | $\beta_1$ |
|---|---|---|---|---|---|---|
| pCI-neo | 760† | 396 | 317 | 309 | 509 | 363 |
|  | 59%* | 62% | 30% | 74% | 59% | 72% |
| IRP-1 | 533 | 364 | 266 | 405 | 469 | 361 |
|  | 51% | 66% | 32% | 74% | 59% | 77% |
| IRP-2 | 711 | 367 | 294 | 384 | 522 | 359 |
|  | 60% | 69% | 38% | 75% | 55% | 76% |
| B2-1 | 666 | 375 | 304 | 418 | 489 | 329 |
|  | 59% | 70% | 36% | 72% | 54% | 73% |
| 14-3-3θ | 690 | 361 | 336 | 368 | 543 | 386 |
|  | 60% | 72% | 43% | 74% | 60% | 75% |

†Mean Fluorescence Intensity
*Percent Positive

As discussed above, different family members can have opposing effects on integrin dependent adhesion. Such opposing effects are consistent with IRPs interacting with different effectors or signaling pathways that regulate integrin binding (discussed below). Redundancy in these pathways may in part explain why overexpression of IRPs results in only a partial block of IL-8 inducible adhesion. In addition, the decrease in adhesion with IRP-1 overexpression may be due to IRP-1 antagonizing a proadhesive activity of another IRP. The proadhesive activity of B2-1 (cytohesin-1) is not unique to JY-8 (Example 5) and has also been observed with overexpression in Jurkat T-lymphoid cells [Kolanus et al., Cell, 86: 233–242 (1996)]. However in contrast to JY-8 cells, expression in Jurkat cells induced $\alpha_L\beta_2$ binding. Thus B2-1 may induce binding of either $\alpha_4\beta_7$ or $\alpha_L\beta_2$ in a cell type specific manner. This is not surprising in that binding properties of a specific integrin can vary with cell type [Chan et al., J. Cell. Biol., 120: 537–543 (1993), Kassner et al., J. Exp. Med., 178: 649–660 (1993)].

Next, subcellular localization of IRP/GFP fusion proteins was determined in JY-8 (Example 5) transfectants adherent to ICAM-1. Glass slides were coated with ICAM-1/Fc (10 μgl/ml) in 50 mM bicarbonate buffer, pH 9.6, for 18 hours at 4° C. and subsequently rinsed with RPMI medium containing 10% FBS. JY-8 transfectants expressing GFP/IRP fusion proteins were allowed to adhere on the ICAM-1 coated glass slides.

To determine the subcellular distribution of IRP/GFP fusion proteins and to identify what regions IRP-1 may be found in intracellular localization, JY-8 transfectants were examined by fluorescence confocal microscopy. IRP-1, IRP-2 and B2-1 localized predominantly to the leading edge cortical cytoskeletal region of cells crawling on ICAM-1 (See Example 8). The PH domain of IRP-1 localized to the plasma membrane region, whereas the Sec7 domain demonstrated a more diffuse cytoplasmic localization. Transfectants expressing GFP demonstrated diffuse cytoplasmic fluorescence. These results indicate that the PH domain, which supports localization to the plasma membrane, functions with other domains to localize wild type IRPs to the leading edge.

To examine the distribution of IRPs during lamelli formation, time-lapse images of JY-8 IRP-2/GFP transfectants crawling on ICAM-1 were analyzed. JY-8 cells overexpressing IRP-2 was chosen to determine localization in cells capable of migrating in response to IL-8 because IRP-2 fusion transfectants demonstrate greater levels of chemotactic migration relative to IRP-1 or B2-1 transfectants. IRP-2 was found concentrated along one edge of JY-8 cells at the site of and prior to lamelli formation. Time lapse images demonstrate that concomitant with its development, IRP-2 relocalized into lamelli. Thus IRP-2 is present very early and throughout lamellipodia extension.

IRPs likely play a role in supporting integrin function in the leading edge of migrating cells. This localization appears to be dependent on both Sec7 and PH domain interactions since the Sec7 domain is diffusely located and the PH domain is uniformly localized to the membrane when expressed independently. PH domain interactions may support a functional membrane localization of a complex containing IRP and ADP ribosylation factor (ARF). At this site ARF can become activated since ARNO (a protein described after filing of the priority application hereto which may be IRP-1) GTP exchange factor (GEF) activity is stimulated by phosphatidylinositol binding to the PH domain [Chardin et al., Nature, 384: 481–484 (1996)]. The role of ARFs in membrane transport suggests that they could mediate integrin localization to and from the leading edge of migrating cells. This would be consistent with the notion that polarized exocytosis in the leading edge may play a critical role in cell locomotion [Bretscher, Cell, 87: 601–606 (1996)].

In addition, an inhibitor of ARF GTP exchange, Brefeldin A, inhibits lamellipodia formation and migration of fibroblasts in a wound healing model [Bershadsky et al., Proc. Natl. Acad. Sci. U.S.A., 91: 5686–5689 (1994)]. B2-1 has been reported to bind directly to the cytoplasmic domain of $\beta_2$ [Kolanus et al., Cell, 86: 233–242 (1996)]. Thus IRPs may link integrins to and activate members of the ras superfamily which might function in one or more steps in chemotaxis.

A role in integrin avidity is also suggested. ARF and another member of the ras superfamily RhoA, act synergistically to activate phospholipase D (PLD) [Kuribara et al., J. Biol. Chem., 270: 25667–25671 (1995)]. PLD is activated by various agonists in different cell types and cleaves phophatidylcholine to produce choline and phosphatidic acid [Boman et al., Trends Bio. Chem. Sci., 20147–150 (1995). Phosphatidic acid, and not various other negatively changed lipids, has been demonstrated to increase binding of purified integrin GPllbllla to fibrinogen [Smyth et al., J. Biol. Chem., 267: 15568–15577 (1992)]. IRPs may function as regulators in signaling pathways that alter integrin membrane localization or avidity. Recently, ARNO has been reported to induce GDP/GTP exchange in, and hence activate a member of the ras superfamily, ARF-1 [Chardin et al., Nature, 384: 481–484 (1996)]. There are six known ARFs and an additional four ARF-like proteins that share 45–60% amino acid identity [Boman et al., Trends in Bio. Chem. Sci., 20: 147–150 (1995)]. ARFs localize to golgi, vesicles and plasma membrane and have been implicated in membrane transport, endocytosis and exocytosis [D'Souza-Schorey et al., Science, 267: 1175–1178 (1995), Peters et al., J. Cell Biol., 128: 1003–1017 (1995), Boman et al., Trends in Biol. Sci., 20: 147–150 (1995)]. IRPs therefore may regulate localized increases in phosphatidic acid that in turn up-regulate integrin binding directly or indirectly through conversion to a PKC agonist diacylglycerol (DAG).

EXAMPLE 5

A JY cell line that stably expresses a functional receptor for IL-8 possessing an N-terminal mAb epitope tag was developed. This cell line is identified herein as "JY-8". To demonstrate a role in $\alpha_L\beta_2$ dependent adhesion, IRPs were overexpressed in the JY-8 cell line. JY-8 cells normally express one $\beta_2$ integrin, $\alpha_L\beta_2$, and one $\alpha_4$ integrin, $\alpha_4\beta_7$ [Chan et al., J. Biol. Chem., 267: 8366–8370 (1992)]. IRP expression constructs were generated with green fluorescence protein (GFP) fused to the amino terminus of IRP-1, IRP-2 and B2-1 wild type sequences as described in the following paragraph.

Expression constructs for green fluorescent protein (GFP) IRP fusion proteins were prepared as follows. The expression vector pCEP4 (Invitrogen, San Diego, Calif.) was digested with Nhe1 and BamHI. A Nhe1 and BamHI digested DNA fragment encoding GFP from pEGFP (Clontech, Palo Alto, Calif.), was ligated to the NHe1/Bam HI digested pCEP4. The resulting plasmid, pCEP4/GFP, was used to make IRP fusion constructs.

To subclone IRP DNA fragments into pCEP4/GFP, PCR reactions were performed to add Xho I and Hind III restriction sites to the ends of the fragments for subsequent in frame ligation.

The following primer pairs were used for PCR: S3.GFP.Xho.5, ATATCTCGAGCTATGGAGGACGGCGTCTAT, (SEQ ID NO: 20) and S3.GFP.H3.3, ATATAAGCTTGCGGCCGCT-CAGGGCTGCTCCTGCTTC (SEQ ID NO: 21) for IRP-1 GFP fusion; S7.GFP.Xho.5, ATATCTCGAGCTATGGAGGAGGACGACAGCTAC, (SEQ ID NO: 22) and S7.GFP.H3.3, ATATAAGCTTGCG-GCCGCTCAGTGTCGCTTCGTGGAGG (SEQ ID NO: 23) for B2-1 GFP fusion; S12.GFP.Xho.5, ATATCTCGAGCTATGGACCTGTGCCACCCAG, (SEQ ID NO: 24) and S12.GFP.H3.3, ATATAAGCTTGCGGCCGCTCACTGCTTGCTGGCAA-TCTTC, (SEQ ID NO: 25) for IRP-2 GFP fusion; S3.GFP.5.X, ATATCTCGAGCTATGAGCGAGGTGGAGGGGCTG, (SEQ ID NO: 26) S3.GFP.5.H3, ATATAAGCTTGCGGCCGCTCAGAAGGTGTGGGTC-AGGTC, (SEQ ID NO: 27) for IRP-1 Sec7 domain GFP fusion; S3.GFP.P.X. ATATCTCGAGCTATGACCTTCTTCAACCCGG, (SEQ ID NO: 28) and S3.GFP.H3.3 for IRP-1 PH domain GFP fusion.

In addition, amino acid substitution mutants were generated using the Muta-Gene Phagemid in vitro mutagenesis kit (Version 2, BioRad, Hercules, Calif.) with the oligonucleotides: S3.E156A, GTCAATTTTCTGGGCCGCTCCGGGTAGGCGAAA, (SEQ ID NO: 29) for preparing E156A and S3.R279A, TGTGAGGATAAACCAGGCCCGCTTCCACGTCTTC (SEQ ID NO: 30) for preparing R279A. PCR amplification of the mutant cDNA using the primers S3.GFP.Xho5 and S3.GFP.H3.3, was performed to generate appropriate restriction sites for GFP fusion.

The resulting PCR products were ligated to the Xho I and Hind III sites of PCEP4/GFP. Clones isolated from E. coli XL1 Blue transformants were confirmed by sequencing. All expression vectors were designed to encode IRP/GFP fusion proteins with GFP at the amino terminus of the fusion protein. JY-8 cells were transfected by electroporation with the expression constructs and the transfectants were selected using hygromycin B (0.5 mg/ml, Calbiochem, San Diego, Calif.).

In addition, IRP-1 GFP fusion proteins having amino acid substitutions in the Sec7 or PH domains were generated. A substitution of alanine for glutamate at position 156, E156/A, was chosen based on the effects of this mutation on cellular adhesion in the Sec7 domain of an Arabidopsis protein, EMB30 [Shevell et al., Cell, 77: 1051–1062 (1994)]. Similarly, a substitution in the PH domain, R279/A, was chosen based on a mutation identified in the PH domain of BTK which results in an X-linked agammaglobulinemia (XLA) [Yao et al., Proc. Natl. Acad. Sci. U.S.A., 91: 9175–9179 (1994)] and may be important in PKC (Yao, et al., Proc. Nat. Acad. Sci, USA, 91: 9175–9179 (1994) and Inositol 1,3,4,5-Tetrakisphosphate ($IP_4$) [Fukuda et al., J. Biol. Chem., 271: 30303–30306 (1996)] binding. Truncates containing either the Sec7 domain or the PH domain of IRP-1 fused to GFP were also generated.

Imunoblotting showed that the IRP/GFP fusion proteins were expressed in all JY-8 transfectants at similar levels. To confirm expression of fusion proteins, detergent lysates of JY-8 transfectants were immunoblotted with antibodies specific for IRP-1, B2-1, IRP PH domains and GFP. The migration of all GFP fusion proteins, in SDS-PAGE, was consistent with their predicted sizes. In addition, fusion proteins bound appropriate IRP-1, B2-1 or PH domain specific mAb as well as GFP antibodies. Endogenous IRP-1 and B2-1 was also detected in JY lysates. Estimates from several blots indicated that all seven fusion proteins were expressed at levels at least ten-fold greater than that of endogenous IRP-1 and B2-1.

Integrin dependent cellular adhesion is inducible by various stimuli [Diamond and Springer, Curr. Opin. Biol., 4: 506–517, (1994)]. Known stimuli for inducing adhesion include agonists for G-protein coupled chemokine receptors such as IL-8 or agonists for PKC such as PMA. These stimuli activate signalling pathways that may regulate cytoskeletal organization and integrin clustering in a manner that increases or stabilizes integrin-dependent adhesion. Chemokines and agonists such as PMA are utilized routinely to increase adhesion or determine maximal levels of adhesion in in vitro assays.

Adhesion assays measuring IRP/GFP fusion proteins binding to ICAM-1 or VCAM-1 were performed in 96-well Easy Wash plates (Corning) using a modified procedure of Morla et al., Nature, 367: 193–196 (1994). Each well was coated with 50 μl of ICAM-1/Fc (5 μg/ml) or VCAM-1/Fc (2 μg/ml) in 50 mM bicarbonate buffer (pH 9.6). Some wells were coated with a CD18 mAb (22F12C, ICOS Corporation) to quantitate 100% of input cell binding or BSA block to determine background binding. Plates were blocked with 1% BSA in PBS for one hour at room temperature. Wells were then rinsed and 200 μl of adhesion buffer (5% FBS, 5 mM KCl, 150 mM NaCl, 1 mM $MgCl_2$, 1 mM $CaCl_2$, 20 mM HEPES, 10 mM D-Glucose) was added with or without PMA (20 ng/ml) or IL-8 (25 ng/ml). JY-8 cells (100 μl of 5×10$^6$/ml) were then added to each well and plates were incubated at 37° C., in 5% $CO_2$ for 5 or 30 minutes. Adherent cells were fixed with the addition of 50 μl of 10% glutaraldehyde solution and stained with 0.5% crystal violet (SIGMA) solution. After washing and the addition of 70% ethanol, adherent cells were quantitated by determining absorbance at 570 nm using a SPECTRAmax™ 250 Microplate Spectrophotometer System (Molecular Devices). Percent adherent cells was determined using the formula:

$$\frac{A_{570}(\text{binding to ICAM-1 or VCAM-1}) - A_{570}(\text{binding to BSA})}{A_{570}(\text{binding to CD18 mAb})} \times 100$$

Adhesion of JY-8 transfectants to immobilized ICAM-1 or VCAM-1 was determined under static conditions with no stimulation (basal level binding) as well as under IL-8 or PMA stimulation. In comparison to basal level binding, JY-8 cells expressing only GFP (control) demonstrated a 3–4 fold increase in binding to ICAM-1 and a 2-fold increase in binding to VCAM-1 in the presence of IL-8. IL-8 inducible adhesion to VCAM-1 was apparent at five minutes, however, an increase in basal level binding between five and thirty minutes decreased the difference between stimulated and unstimulated binding. Subsequent assays were performed for thirty minutes. PMA treatment resulted in a 4-fold or greater increase in adhesion to ICAM-1 and VCAM-1. JY-8 transfectants overexpressing IRP-1 demonstrated a 40–50% decrease in binding to ICAM-1 relative to control transfectants expressing equivalent or greater levels of GFP. This decrease was apparent for basal and IL-8 stimulated adhesion, but not for PMA induced adhesion. The binding of the IRP-1 overexpressing JY-8 transfectants to VCAM-1 was also decreased by approximately 40% under conditions of IL-8 stimulation, but not basal or PMA stimulated conditions. These results indicate that IRP-1 preferentially effects chemokine but not PMA stimulated adhesion and that IRP-1 overexpression does not render cells generally adhesion incompetent.

To determine the contribution of different IRP-1 domains to the inhibition of adhesion, JY-8 cells expressing the amino acid substitution and deletion mutants were tested. Substitution of amino acids in the Sec7 and PH domains abrogated the effects of IRP-1 overexpression on adhesion. Transfectants expressing the IRP-1 Sec7 domain mutation E156/A, and the PH domain mutation R279/A, demonstrate levels of binding to ICAM-1 and VCAM-1 equivalent to that of GFP expressing JY-8. In addition, expression of IRP-1 Sec7 or PH domains independently did not decrease binding to either ICAM-1 or VCAM-1 as effectively as wild type IRP-1. Thus, both Sec7 and PH domains function together to regulate IL-8 stimulated adhesion to ICAM-1 and VCAM-1.

In addition to IRP-1, the effects of IRP-2 and B2-1 overexpression on JY-8 adhesion was determined. JY-8 transfectants overexpressing IRP-2 demonstrated a weak decrease, approximately 20%, in basal level binding to ICAM-1 or IL-8 induced binding to ICAM-1 and VCAM-1 relative to GFP transfectants. In contrast, transfectants overexpressing B2-1 demonstrated control levels of IL-8 stimulated binding to VCAM-1 but consistently increased binding to VCAM-1 by approximately 50%. Thus, the effects on B2-1 overexpression in IL-8 stimulated adhesion to VCAM-1 is opposite to that of IRP-1 and IRP-2 and selective for $\alpha_4\beta_7$/VCAM-1 interaction.

The modulation of JY-8 adhesion to ICAM-1 and VCAM-1 with overexpression of IRPs cannot be attributed to changes in cell surface levels of $\alpha_L\beta_2$ or $\alpha_4\beta_7$. There was relatively little difference in the amount of expression of $\alpha_L\beta_2$ or $\alpha_4\beta_7$ on different JY-8 transfectants overexpressing IRPs relative to the transfectant expressing GFP. JY-8 cells overexpressing IRP-1 Sec7 displayed a moderately decreased expression of $\alpha_4\beta_7$, nevertheless, these cells did not show decreased adhesion to VCAM-1.

EXAMPLE 6

The integrin $\alpha_4\beta_7$ can mediate attachment and rolling adhesion of lymphocytes to the endothelial cell ligands VCAM-1 and MadCAM-1 under flow conditions [Berlin, et al., supra (1995)]. In order to determine if IRP expression effects $\alpha_4\beta_7$ mediated cell attachment and rolling, binding of JY transfectants under flow conditions was quantitated [Berlin, et al., supra (1995)]. In addition, cell binding under flow conditions was examined following static adhesion to determine possible changes in $\alpha_4\beta_7$ avidity resulting from IRP expression.

Figure 2:
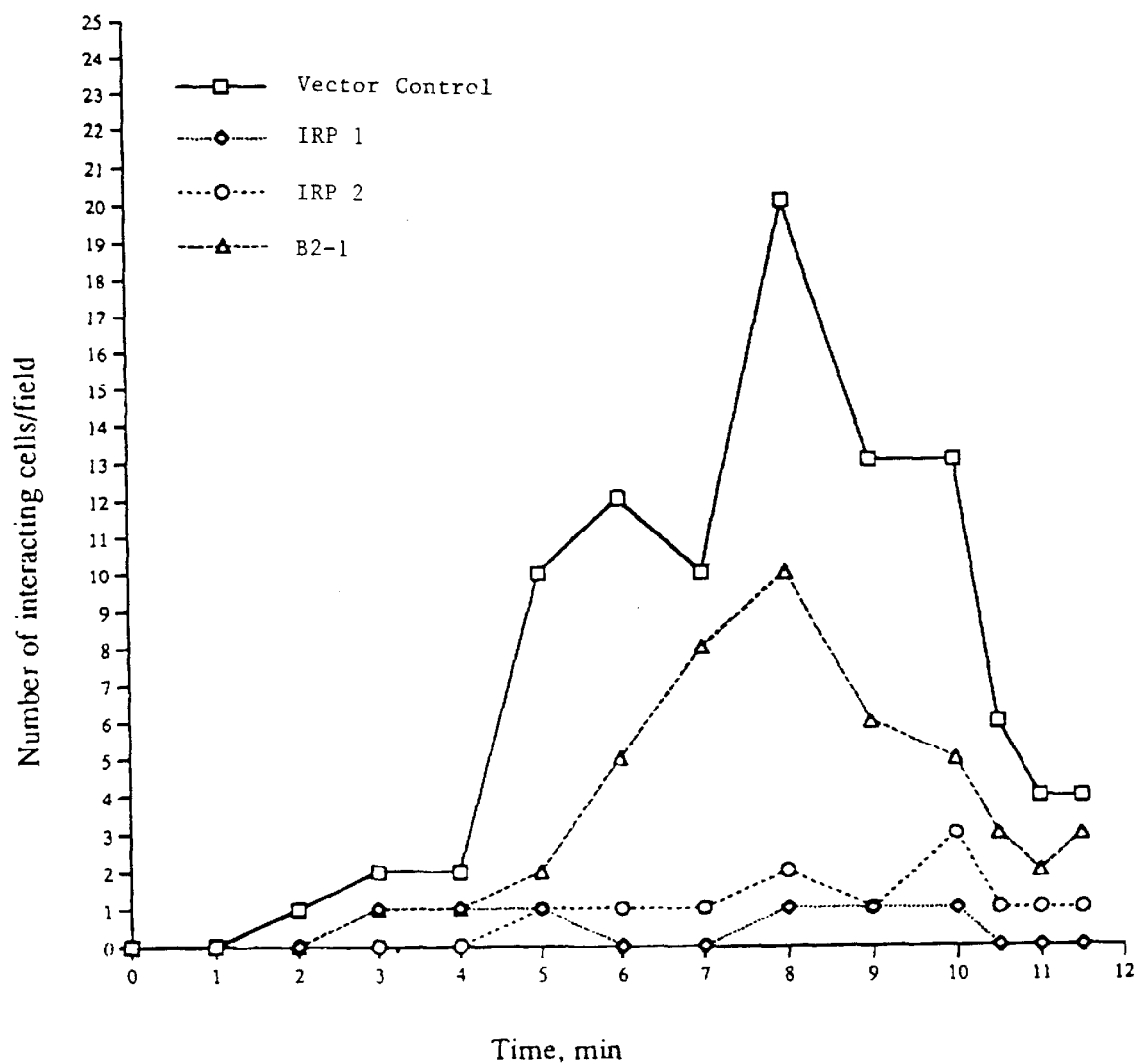
FIG. 2 presents a graph showing the ability of JY cells, expressing the indicated polypeptides, to bind to ICAM-1.

JY cells, which express endogenous $\alpha_4\beta_7$, were transfected with either full length IRP-1 ($JY_{IRP-1}$), IRP-2 ($JY_{IRP-2}$), or B2-1 ($JY_{B2-1}$) encoding sequences or vector control DNA ($JY_{VEC}$) and introduced into a flow system loop containing an immobilized VCAM-1/immunoglobulin (VCAM-1/Ig) chimeric protein [Vonderheide, et al., *J. Cell. Biol.* 125: 215–222 (1994)]. The initial flow rate was 3 dynes/cm$^2$ which was maintained for one minute. For the next five minutes, the flow rate was reduced to 1.5 dynes/cm$^2$, during which time $JY_{VEC}$ transfectants and to a lesser extent, $JY_{B2-1}$ transfectants demonstrated the ability to attach and roll (FIG. 2). Cells transfected with either IRP-1 or IRP-2, $JY_{IRP-1}$ and $JY_{IRP-2}$, did not or very rarely attached.

For the next minute, transfected cells were incubated in the presence of the immobilized ligand in the absence of flow, and this time was insufficient to permit $JY_{IRP-1}$/VCAM-1 or $JY_{IRP-2}$/VCAM-1 binding. After the period of static binding, the flow rate was incrementally increased from 1.5 to 9 dynes/cm$^2$ over the next four and a half minutes. Binding of $JY_{B2-1}$ and $JY_{VEC}$ both decreased as the flow rate reached 3 dynes/cm$^2$ (FIG. 2). The similar decreasing rates of binding for the two proteins suggest similar binding avidities for IRP-3 and VEC.

The results of the assay indicate that IRP-1 and IRP-2 expression abrogate the ability of $\alpha_4\beta_7$ to bind to VCAM-1 under both flow and short term static conditions. Expression of B2-1, however, appears to only decrease the efficiency of attachment and rolling.

In order to determine the effect of IRP-1 and IRP-2 expression on the binding of endogenous LFA-1 to ICAM-1, JY cells transfected as described above were utilized in a similar assay except that ICAM-1 was the immobilized counterreceptor. All of the transfected JY cells except $JY_{B2-1}$ cells attached and rolled on ICAM-1 at 1.5 dynes/cM$^2$. The efficiency of attachment, however, was reduced relative to $\alpha_4\beta_7$/VCAM-1 binding (FIG. 1). Adhesion to ICAM-1 increased markedly following one minute of static binding for all transfectants except $JY_{IRP-1}$ cells, for which binding increased but to a lower maximum. As the flow rate was increased following static binding, ICAM-1 binding of $JY_{IRP-1}$, $JY_{B2-1}$ and $JY_{VEC}$ cells decreased. $JY_{IRP-2}$ cell binding, however, appeared to be most resistant to increasing flow rates as binding was detected at a flow rate up to 7.5 dynes/cm$^2$. These results suggest that B2-1 expression abrogates LFA-1 attachment to ICAM-1 under flow conditions; IRP-1 expression decreases LFA-1/ICAM-1 binding under static conditions; and IRP-2 expression supports higher avidity binding between LFA-1 and ICAM-1.

EXAMPLE 7

To generate IRP-1 and B2-1 specific monoclonal antibodies, mice were immunized with His-tagged IRP-1 and B2-1 expressed and purified from E. coli. The coding regions of IRP-1 and B2-1 were ligated in frame into pET15b (Novagen, Madison, Wis.) C-terminal to sequences encoding the histidine tag so that the IRP-1 and B2-1 proteins were expressed as N-terminal histidine tagged proteins in E. coli strain BL21lysS. Recombinant proteins were purified by standard procedures (Qiagen, Chatsworth, Calif.).

Hybridomas were generated as described generally in Tjoelker et al., J. Biol. Chem., 270: 25481–25487 (1995). For hybridoma series 200, each of five 6 to 12 week old Balb/c mice was pre-bled on day 0 and then immunized subcutaneously with 67 μg E. coli produced HisB2-1, emulsified in complete Freunds adjuvant. On day 21, each mouse was boosted with 25 μg HisB2-1 in incomplete Freunds adjuvant. Test bleeds were taken on day 34 and tested by western blot. 100 ng HisB2-1 protein from a 10% reducing SDS-PAGE was transferred onto PVDF, which was then cut into strips. The blot was blocked for one hour at ambient temperature with 3% BSA, 0.2% Tween 20 in CMF-PBS. Pre-immune and immune sera were diluted 1:500 in blocking buffer and incubated with the strips for two hours at ambient temperature. Strips were washed three times with 2% Tween 20 in CMF-PBS and then incubated with goat anti-mouse (Fc)-HRP for one hour. After washing four times, strips were developed with Renaissance chemiluminescent reagents (NEN). Mouse #2413 was given a final intraperitoneal boost of 25 μg HisB2-1 protein in CMF-PBS on day 45 and the spleen was removed four days later.

For hybridoma series 233, each of five 6 to 12 week old Balb/c mice was pre-bled on day 0 and the immunized subcutaneously with 30 μg E. coli produced HisIRP-1, emulsified in complete Freunds adjuvant. On day 22, each mouse was boosted with 10 μg HisIRP-1, and on Day 45 with 5 μg HisIRP-1, in incomplete Freunds adjuvant. On day 55, test bleeds were taken and tested by western blot against HisIRP-1 and HisIRP-2. Mouse #2520 was boosted intraperitoneally with 50 μg HisIRP-1 in CMF-PBS each day on days 133 and 134, and the spleen was sterilely removed on day 137.

Fusions were performed as described below. Briefly, a single-cell suspension was formed by grinding the spleen between the frosted ends of two glass microscope slides submerged in serum free RPMI 1640, supplemented with 2 mM L-glutamine, 1 mM sodium pyruvate, 100 units/ml penicillin, and 100 μg/ml streptomycin (RPMI) (Gibco, Canada). The cell suspension was filtered through sterile 70-mesh Nitex cell strainer (Becton Dickinson, Parsippany, N.J.) and washed twice by centrifuging at 200 g for five minutes and resuspending the pellet in 20 ml serum free RPMI. Thymocytes taken from three naive Balb/c mice were prepared in a similar manner.

NS-1 myeloma cells, kept in log phase in RPMI with 11% FetalClone serum (FBS) (Hyclone Laboratories, Inc., Logan, Utah) for three days prior to fusion, were centrifuged at 200 g for five minutes, and the pellet was washed twice as described in the foregoing paragraph. After washing, each cell suspension was brought to a final volume of 10 ml in serum free RPMI and counted.

Spleen cells were combined with NS-1 cells in a ratio of 5:1, centrifuged and the supernatant was aspirated. The cell pellet was dislodged and 2 ml of 37° C. PEG 1500 (50% in 75 mM Hepes, pH 8.0) (Boehringer Mannheim) was added while stirring over the course of one minute, followed by addition of 14 ml of serum free RPMI over seven minutes. An additional 16 ml RPMI was added and the cells were centrifuged at 200 g for ten minutes. After discarding the supernatant, the pellet was resuspended in 200 ml RPMI containing 15% FBS, 100 μM sodium hypoxanthine, 0.4 μM aminopterin, 16μM thymidine (HAT) (Gibco), 25 units/ml IL-6 (Boehringer Mannheim) and 1.5×10⁶ thymocytes/ml. The suspension was dispensed into ten 96-well flat bottom tissue culture plates (Corning, United Kingdom) at 200 μl/well. Cells in plates were fed three to five times before screening by aspirating approximately 100 μl from each well with an 18 G needle (Becton Dickinson), and adding 100 μl/well plating medium described above except containing 10 units/ml IL-6 and lacking thymocytes.

Supernatants from fusion 200 were screened initially by ELISA on the immunogen and detected with goat anti-mouse IgG (fc) horse radish peroxidase conjugate. Supernatants from thirty wells that gave the highest signal were retested by Western analysis on the immunogen. Based on assay results, nine fusion wells were selected for further cloning. The nine wells were designated 200A through 200I.

Supernatants from fusion 233 were initially tested by ELISA on HisIRP-1 and HisB2-1 coated plates. Fusions from wells reacting with HisIRP-1 and not HisB2-1 were selected for further cloning.

These fusion cells were subcloned successively using RPMI, 15% FBS, 100 μM sodium hypoxanthine, 16 uM thymidine, and 10 units/ml IL-6. Subcloning was performed either by doubling dilution or by limiting dilution, by seeding 96 well plates at 0.5–1.0 cells/well. Wells of subclone plates were scored visually and the numbers of colonies in the least dense wells were recorded. Selected wells of each cloning were tested, by ELISA or Western blot as described, for reactivity observed in the original fusion well. Cloning was completed for cell lines 200A, 200B, 200F, 200H, 200G, 233E, 233G, and 233K. Western blots were performed by reacting antibodies from the eight hybridoma lines with IRP-1, IRP-2, and B2-1. Isotypes were determined for the monoclonal antibodies from the eight hybridoma cell lines using either the Isostrip kit (Boehringer Mannheim) or an ELISA using isotype specific reagents (Zymed Laboratories, South San Francisco, Calif.). All antibodies are IgG1 except 200G which is IgG2a isotype.

Hybridoma cell lines 200A, 200B, and 233G were deposited with the American Type Culture Collection.

The 233 series of mAbs were further tested by using hybridoma supernatants to screen in Western blots. Briefly, JY-8 cells transfected with either GFP/IRP-1, GFP/IRP-2 or GFP/B2-1 (see Example 5) were lysed in 1% CHAPS buffer. Cells were lysed on ice for thirty minutes and then centrifuged at 12,000 rpm for ten minutes. Sample buffer was added to the supernatants and the samples were boiled for four minutes. Samples were run on an 8% Novex gel and transferred to PVDF membrane. The membrane was blocked in TST (25 mM Tris pH 8.0, 150 mM NaCl, 0.2% Tween-20) containing 3% BSA for one hour. Blocking solution was removed and replaced with a 1:20 dilution of hybridoma supernatant in binding buffer (3% BSA in TST) and incubated at room temperature for one hour. The membrane was washed extensively with TST and then incubated with an HRP conjugated goat anti-mouse IgG Fc fragment (Jackson ImmunoResearch) for thirty minutes at room temperature. After washing with TST, a Renaissance kit (NEN) was used for ECL detection and the membrane was exposed to Hyperfilm (Kodak). Supernatants from 233A, 233D, 233G, 233K, and 233L all specifically recognized an appropriately sized 77 kDa band in the GFP-Irp-1 lysate and not in the GFP-IRP-2 or GFB-B2-1 lysates. The signal using 233G was strongest.

Using the same procedures as above, purified 200A and 200B mAbs were tested for their ability to detect GFP-IRP fusion proteins from lysates of JY-8 transfectants using Western blotting. Both mAbs were used at 1 μg/ml in Western blotting. mAb 200A recognized GFP-Irp-1, GFP-IRP-2 and GFP-B2-1 equally well, whereas 200B preferentially recognized GFP-B2-1 and showed weak recognition (less than 10% of the level seen with B2-1) of GFP-Irp-1. On another Western containing lysate of a JY-8 transfectant expressing a GFP tagged PH domain of an IRP-1 truncation, 200A detected a band of an appropriate size for a GFP-IRP-1 PH domain truncate suggesting that 200A recognizes a common epitope in the homologous PH domains of IRP-1, IRP-2 and B2-1.

Hybridoma supernatants were screened for specific reactivity to recombinant proteins by ELISA. In addition, specificity was determined by reactivity to Western blots containing IRP-1, IRP-2 and B2-1 *E. Coli* expressed proteins. mAb 200A (reactive to IRP-1, IRP-2 and B2-1 PH domains), 233G (reactive to IRP-1) and 200B (reactive to B2-1) were used to determine expression levels and sizes of GFP-IRP fusion proteins in JY-8 IRP transfectants.

To determine integrin expression levels on JY-8 transfectants, cells were stained with mAb specific for $\alpha_L\beta_2$, TS1/22 (ATCC), and $\alpha_4$, IC/A4.1 (ICOS Corporation) by standard indirect immunofluorescence. Fluorescence was quantitated by flow cytofluorometry using a FACS scan.

EXAMPLE 8

Chemotaxis requires not only initial adhesion to substrate and cycling of integrin through phases of binding and release in polarized cells but also requires recycling of integrin from the trailing to the leading edge. To determine if IRPs effect other integrin functions in addition to static adhesion, the role of IRP on chemotaxis was determined by a chemotactic cell migration assay. In this assay, JY-8 cells migrate toward a source of IL-8 in an integrin and CAM dependent manner.

The assay was a modification of a procedure for cell migration under agarose as described by Schreiner et al., *Immunol.*, 88: 89–96 (1980). Briefly, 6-well plates (Falcon) were coated with either ICAM-1/Fc (25 μg/ml) or VCAM-1/Fc (10 μg/ml) (ICOS Corporation) in bicarbonate buffer (pH 9.6). After overlaying 1% agarose in RPMI containing 0.5% BSA (Intergen) plates were incubated at 4° C. for 30 minutes. Cells were washed with RPMI and resuspended at $5 \times 10^7$/ml in RPMI with 0.5% BSA. Wells were formed in the agarose by using a 2.5 mm gel puncher (Pharmacia), and filled immediately with 10 μl of either IL-8 (2.5 μg/ml) (PeproTech) or cell suspension. Plates were incubated at 37° C. in 5% $CO_2$ for 8 hours. Cells were then fixed by the addition of 2% glutaraldehyde solution. After removing the agarose, wells were rinsed with $dH_2O$ and dried. Quantitation of cell migration was performed using a video microscopy work station consisting of a Diaphot microscope (Nikon, Tokyo, Japan), a CCD-72 video camera and DSP2000 digital processor (Dage, Michigan City, Ind.), and a Macintosh® NIH Image program (developed at the U.S. National Institutes of Health and available from the Internet by anonymous FTP from zippy.nimh.nih.gov or on floppy disk from the National Technical Information Service, Springfield, Va., part number PB95-500195GEI).

Cheomotaxis of JY-8 cells expressing GFP/IRP fusion proteins was determined as described above. IRP-1, IRP-2 and B2-1 overexpression in JY-8 cells decreased chemotaxis on ICAM-1 or VCAM-1 relative to GFP expressing transfectants. Expression of the IRP-1 PH domain substitution mutant R279/A also decreased chemotaxis. However, expression of R279/A decreased chemotaxis much less effectively then expression of wild type IRP-1. Expression of the IRP-1 PH domain also decreased chemotaxis on ICAM-1 and VCAM-1. These results indicate that IRP-1 PH domain plays a major role in the IRP-1 mediated decrease in chemotaxis. The substitution E156/A in IRP-1 Sec7 domain also resulted in a decrease in chemotaxis but less than that observed with wild type IRP-1 overexpression. Overexpression of IRP-1 Sec7 domain resulted in increased chemotaxis on ICAM-1, but no change in chemotaxis was observed on VCAM-1. These results indicate that the Sec7 domain can also contribute to chemotaxis. Thus both IRP-1 Sec7 and PH domains function in $\alpha_4\beta_7$ and $\alpha_L\beta_2$ dependent chemotactic migration.

As discussed above, the inhibitory effect of IRP-1 overexpression on chemotaxis was decreased by substitutions in the Sec7 (E156/A) and PH (R279/A) domains, indicating that as with adhesion both domains contribute to IRP-1 regulation of chemotaxis. The increased chemotactic migration of JY-8 transfectants expressing IRP-1 R279/A relative to wild type, and the near complete blocking with expression of the IRP-1 PH domain, indicates that the PH domain plays a major role in chemotaxis. Therefore interactions between IRP-1 PH domain and phosphatidylinositols [Harlan et al., *Biochemistry*, 34: 9859–9864 (1995), Pitcher et al., *J. Biol. Chem.*, 270: 11707–11710 (1995)] or heterotrimeric G protein βγ subunits [Mahadeven et al., *Biochemistry*, 34: 9111–9117 (1995), Touhara et al., *J. Biol. Chem.*, 269: 10217–10220 (1994), Pitcher et al., *J. Biol. Chem.*, 270: 11707–11710 (1995)] appear to be critical to the role of IRPs in chemotaxis.

EXAMPLE 9

Tissue distribution of IRPs was determined using monoclonal antibodies 200B and 233G. Antibody 200B preferentially recognizes B2-1 and antibody 233G specifically recognizes IRP-1.

Both monoclonal antibodies were used at 10 μg/ml for immunocytochemical analysis of frozen human tonsil, spleen, and lymph node sections. Sections of 6 micron thickness were layered onto Superfrost Plus Slides (VWR) and stored at −70° C. Prior to use, slides were removed from −70° C. and placed at 55° C. for five minutes. Sections were then fixed in cold 4% paraformaldehyde for two minutes, then in cold acetone for 5 minutes and air dried. Sections were blocked in a solution containing 1% BSA, 30% normal human sera and 5% normal rat sera for thirty minutes at room temperature. Antibodies 200B or 233G was applied to each section for one hour at room temperature. Unbound antibody was removed by washing the slides three times in TBS buffer for five minutes per wash. Next, rat anti-mouse-biotin conjugated antibody was applied to each section in the same TBS buffer and incubated for thirty minutes at room temperature. An ABC-elite kit (Vector Labs) was used to detect the secondary antibody and was applied to each section for thirty minutes at room temperature. DAB substrate (Vector Labs) was applied and color development stopped by immersion in water. The color was enhanced by the application of 1% Osmic Acid for approximately five to ten seconds. The enhancement was stopped by placing slides in water. Sections were counter stained in Hematoxylin Gill's No. 2 and rinsed in water, acid alcohol, lithium carbonate before dehydration and mounting with Permount (VWR). 200B and 233G staining was detected in tonsil, spleen, and lymph node, but not with a control IgG1 antibody.

Both antibodies displayed very strong labeling on the mucosal epithelium on tonsil. Both antibodies appear to be labeling a subset of stratified squamous epithelium. A difference between 200B and 233G binding in the tonsil is the labeling seen within the secondary follicles with 233G. This labeling was not seen with 200B. In the spleen, both antibodies looked very similar in their binding, labeling individual cells in the red pulp areas. In the lymph node, binding was observed on individual cells in the deep cortex with 200B and in the deep cortex and medullary cortex with 233G. The labeling pattern seen with 200B was very punctate. This was also seen with 233G but it was much more subtle.

EXAMPLE 10

PH domains are present in over seventy functionally diverse proteins including kinases and linker proteins. PH domains have been reported to confer the ability to bind to G protein $_{\beta\gamma}$ subunits, $PIP_2$, and PKC. The SEC7 motif in IRPs also occurs in other proteins not sharing homology beyond this motif and is likely to support intramolecular interactions. In addition, the kinesin/myosin amino terminal homology of IRPs might similarly be predicted to support interaction with other proteins. Proteins which interact with IRPs may be identified by various assays as described below.

A first assay contemplated by the invention is a two-hybrid screen. The two-hybrid system was developed in yeast [Chien et al., *Proc. Natl. Acad. Sci.* (*USA*), 88: 9578–9582 (1991)] and is based on functional in vivo reconstitution of a transcription factor which activates a reporter gene. Specifically, a polynucleotide encoding a protein that interacts with IRPs is isolated by: transforming or transfecting appropriate host cells with a DNA construct comprising a reporter gene under the control of a promoter regulated by a transcription factor having a DNA binding domain and an activating domain; expressing in the host cells a first hybrid DNA sequence encoding a first fusion of part or all of IRPs and either the DNA binding domain or the activating domain of the transcription factor; expressing in the host cells a library of second hybrid DNA sequences encoding second fusions of part or all of putative IRPs binding proteins and the DNA binding domain or activating domain of the transcription factor which is not incorporated in the first fusion; detecting binding of an IRPs interacting protein to IRPs in a particular host cell by detecting the production of reporter gene product in the host cell; and isolating second hybrid DNA sequences encoding the interacting protein from the particular host cell. Presently preferred for use in the assay are a lexA promoter to drive expression of the reporter gene, the lacZ reporter gene, a transcription factor comprising the lexA DNA binding domain and the GAL4 transactivation domain, and yeast host cells.

Other assays for identifying proteins that interact with IRPs may involve immobilizing IRPs or a test protein, detectably labelling the nonimmobilized binding partner, incubating the binding partners together and determining the amount of label bound. Bound label indicates that the test protein interacts with IRPs.

Another type of assay for identifying IRPs interacting proteins involves immobilizing IRPs or a fragment thereof on a solid support coated (or impregnated with) a fluorescent agent, labelling a test protein with a compound capable of exciting the fluorescent agent, contacting the immobilized IRPs with the labelled test protein, detecting light emission by the fluorescent agent, and identifying interacting proteins as test proteins which result in the emission of light by the fluorescent agent. Alternatively, the putative interacting protein may be immobilized and IRPs may be labelled in the assay.

EXAMPLE 11

Modulators of IRP interactions are contemplated by the invention as useful in decreasing integrin, especially $\beta_2$ and/or $\beta_7$ integrin, adhesion to cellular or extracellular matrix ligands resulting in down regulation of functions supported by integrin engagement, especially cell growth, stimulation, and localization in inflammatory processes. Specifically, it is contemplated that the modulators have therapeutic value in treatment of inflammatory or autoimmune diseases by decreasing the influx of cells, for example neutrophils, eosinophils, lymphocytes, monocytes or NK cells, to an inflammatory site and diminishing the cytotoxic activity of cells already localized to such a site. Modulators may be able to both down regulate integrin dependent adhesion and antagonize stimulatory and costimulatory activities of integrins. Modulators of IRPs may have an advantage over compounds that interfere with integrin binding to extracellular ligands (i.e., blocking antibodies or extracellular ligand antagonists) because engagement of integrins can have activating effects and be proinflammatory. Modulators of IRP binding may directly or indirectly disrupt integrin signaling pathways. Because overexpression of the carboxy terminal PH domain of IRPs does not appear to result in an integrin specific decrease in cell adhesion, specificity may be a function of amino terminal sequences that possess kinesin or SEC7 homologies. Thus, modulators that bind to these amino terminal sequences may effect cellular adhesion in an integrin specific manner. Examples of assays for identifying compounds that modulate interaction of IRPs with other proteins are set out below.

A first assay involves transforming or transfecting appropriate host cells with a DNA construct comprising a reporter gene under the control of a promoter regulated by a transcription factor having a DNA-binding domain and an activating domain; expressing in the host cells a first hybrid DNA sequence encoding a first fusion of part or all of IRPs and the DNA binding domain or the activating domain of the transcription factor; expressing in the host cells a second hybrid DNA sequence encoding part or all of a protein that interacts with IRPs and the DNA binding domain or activating domain of the transcription factor which is not incorporated in the first fusion; evaluating the effect of a test compound on the interaction between IRPs and the interacting protein by detecting binding of the interacting protein to IRPs in a particular host cell by measuring the production of reporter gene product in the host cell in the presence or absence of the test compound; and identifying modulating compounds as those test compounds altering production of the reported gene product in comparison to production of the reporter gene product in the absence of the modulating compound. Presently preferred for use in the assay are a lexA promoter to drive expression of the reporter gene, the lacZ reporter gene, a transcription factor comprising the lexA DNA binding domain and the GAL4 transactivation domain, and yeast host cells.

Another type of assay for identifying compounds that modulate the interaction between IRPs and an interacting protein involves immobilizing IRPs or a natural IRPs interacting protein, detectably labelling the nonimmobilized binding partner, incubating the binding partners together and determining the effect of a test compound on the amount of label bound wherein a reduction in the label bound in the present of the test compound compared to the amount of label bound in the absence of the test compound indicates that the test agent is an inhibitor of IRPs interaction with protein. Conversely, an increase in the label bound in the presence of the test compound compared to the amount label bound in the absence of the compound indicates that the putative modulator is an activator of IRP interaction with the protein.

Specifically, IRP proteins were expressed as His-tagged or His-kemptide-tagged recombinant proteins and were purified over metal chelating chromatography resins from pET15b-transformed *E. coli* lysates.

A well known means for radiolabeling recombinant proteins is to tag the peptide with a kemptide tag. The kemptide tag is a seven amino acid polypeptide fragment which contains a protein kinase A (PKA) phosphorylation site. The kemptide tagged recombinant protein may be radiolabeled at the kemptide tag by the action of PKA [Mohanraj, et al., *Protein Expr. Purif* 8(2): 175–182 (1996).

IRPs (non-kemptide-tagged) were radiolabeled with free $^{125}$I either by the Iodobead® method (Pierce) or using the lactoperoxidase/hydrogen peroxide method modified from *Antibodies, A Laboratory Manual*, Cold Spring Harbor Laboratory, Harlow and Lane, Editors, Chapter 9, pages 319–358 (1988). The radiolabeled proteins were desalted and stored in binding assay buffer was either 20 mM HEPES or 20 mM sodium phosphate pH 7.5 buffers with either 150 mM or 300 mM NaCl, with or without 0.05% detergent (NP-40 or Triton-X-100), and 2 mM azide as preservative. Final specific radioactivity was between 3–10 $\mu$Ci [$^{125}$I]/nmol IRP.

$\beta_2$ integrin cytoplasmic tail proteins (C-tails) were expressed and purified as recombinant His3E9-tagged proteins from either pET15b-transformed *E. coli* or from transformed Saccharomyces sp., or were obtained as untagged, synthetic peptide preparations (Anaspec, Inc. San Jose, Calif., Macromolecular Resources, Fort Collins, Colo.).

The integrin C-tails were immobilized onto 96-well microtiter Scintistrip™ (Wallac) plates at concentrations between 1–100 $\mu$g/ml in volumes of 50–100 $\mu$l bicarbonate, pH 9.6, per well and were incubated at 4° C. overnight. Plates were dried and blocked in 350 $\mu$l/well sterile-filtered 1–2% Bovine Serum Albumin (BSA) dissolved in binding assay buffer and were incubated at room temperature for 1–2 hours. The wells were washed 3 times in binding assay buffer and dried just prior to addition of IRPs.

The binding assay format was either a competition/inhibition binding assay or a saturation binding assay. In the competition binding assay, radiolabeled IRPs were diluted to 25–100 nM in binding assay buffer with one potential modulator of binding (unlabelled IRPs, soluble C-tails or non-specific control polypeptides such as BSA). The assay was initiated with addition of 100 $\mu$l labeled IRPs/potential modulator solution to the blocked Scintistrip™ wells (50, 000–200,000 cpm/well), then incubated one hour at room temperature (22–24° C.) and stopped by rapidly washing in binding assay buffer three to five times. The saturation binding assays were performed similarly, except that a constant 1:20 ratio of radiolabeled:unlabeled IRPs were tested over a total concentration range of 0.01–30 $\mu$M. The plates were dried and scintillation was measured on a Wallac Model 1450 liquid scintillation counter after the detectors were normalized. Interwell crosstalk was corrected for with a test Scintistrip™ plate, containing in the G11, 100 $\mu$l of 25–100 nM radiolabeled IRP captured by anti-IRP monoclonal antibody 200A coated in the well at 20 $\mu$g/ml in bicarbonate buffer. The incubation times and conditions for the test plate were identical to the binding assay above.

Binding was measured as counts of radiolabeled IRPs found in C-tail-coated wells above counts found in BSA-coated wells. Specific binding was assessed as counts found in C-tail-coated wells which were reduced with added unlabelled IRPs or soluble C-tails.

The competition binding assay utilizing iodinated IRP-1 showed that the potential modulators IRP-1, IRP-1 Sec7 domain, B2-1, inhibited binding between iodinated IRP-1 and immobilized His3E9-tagged $\beta_2$ C-tails. IRP-1, IRP-1 Sec7 domain, B2-1, when present in concentrations ranging from 0.001 to 4 $\mu$M decreased the binding of iodinated IRP-1 to the $\beta_2$ C-tail by about 75%. The addition of control peptide (BSA) did not decrease IRP-1 binding to the immobilized $\beta_2$ C-tail. Additionally, a second control in which no $\beta_2$ C-tail was immobilized on a BSA blocked microtiter plate showed only background levels of radiolabeled IRP-1 binding.

The binding assays may be modified by utilizing IRPs and the C-tails of other integrins, including but not limited to $\beta_1$, $\beta_3$ and $\beta_7$. The IRPs or the C-tails can be labeled with [$^3$H]-sodium borohydride, [$^{125}$I]-Bolton-Hunter reagent, [$^{35}$S]-metabolic labelling, protein kinase [$^{32}$P]-labelling, or other suitable radiolabel crosslinking methods. Proteins and peptides may be immobilized on to microtiter plates (Nunc Covalink, Pierce Reactibind, Costar Labcoat, etc . . . ) or to beads (SPA or otherwise). The binding assays may be modified by a skilled artisan to adjust incubation times and modify buffer conditions. In addition, the polypeptides utilized in the assay may include different synthetic peptide fragments and may be prepared by various means understood by the skilled worker, including expression of cDNA constructs, isolation from natural sources and chemical synthesis. The determination that a test compound is a modulator is accomplished by the addition of the test compound to the binding assay. As discussed above, an increase or decrease in binding indicates that the test compound is a modulator of IRPs.

Other binding assays contemplated to be useful in identifying modulators of IRP activity include assays which determine the binding of IRPs to a binding partner (ARFs, phosphatidyl inositols or other related compounds). In these assays, IRP or its binding partner is immobilized to microtiter plates of beads. The amount of binding of detectably labeled IRP or the binding partner is determined in the presence and absence of a test compound under appropriate conditions. A modulator of IRP activity is a compound that decreases or increases the binding of IRP to the binding partner.

To determine the binding of IRP to a phosphatidyl inositol, His-tagged IRP-1 PH domain (5'HA IRP-1 PH) was immobilized on a microtiter plate by incubating 100 $\mu$l of 20 $\mu$g/ml 5'HA IRP-1 PH in bicarbonate buffer, pH 9.6 for approximately sixteen hours at 4° C. The microtiter plate was then decanted and blocked with 1–2% human IgG for one hour at approximately 22° C. The plates were washed three times in assay buffer (25 mM Tris pH 7.4, 100 $\mu$M NaCl, 0.25% NP-40, 0.1% sodium deoxycholate, 1 mM MgCl$_2$, 0.5% DTT). Ten nanomoles of $^3$H-inositol phosphates (IPn) (Du Pont, NEN) was added in 100 $\mu$l assay buffer with between 0–100 $\mu$moles cold IPn for two hours at 22° C. The microtiter plates were washed four times and scintillant was added. The binding was determined by measuring the bound radioactivity in a scintillation counter. The results indicated that His-tagged IRP-1 PH domain bound to inositol (1,3,4,5)$P_4$ and $IP_6$ by a factor of ten over controls. A modulator of binding between IRP and inositol phosphates may be determined by the addition of a test compound to this assay and determining the differences in binding in the presence and absence of the test compound.

Yet another method contemplated by the invention for identifying compounds that modulate the binding between IRPs and an interacting protein involves immobilizing IRPs or a fragment thereof on a solid support coated (or impregnated with) a fluorescent agent, labelling the interacting protein with a compound capable of exciting the fluorescent agent, contacting the immobilized IRPs with the labelled interacting protein in the presence and absence of a test compound, detecting light emission by the fluorescent agent, and identifying modulating compounds as those test compounds that affect the emission of light by the fluorescent agent in comparison to the emission of light by the fluorescent agent in the absence of the test compound. Alternatively, the IRPs interacting protein may be immobilized and IRPs may be labelled in the assay.

Combinatorial libraries, peptide and peptide mimetics, defined chemical entities, oligonucleotides, and natural product libraries may be screened for activity as modulators in assays such as those described above.

EXAMPLE 12

Identification of modulators of IRPs interactions is facilitated by clearly defining the portions of the proteins which are necessary for binding. Amino acid substitution, through standard mutagenesis techniques, is contemplated for use in identifying binding regions of the proteins. Deletion analysis, wherein truncated forms of the proteins are generated, for example by PCR, is also useful for identification of binding regions if the deletion does not disrupt the tertiary or quaternary structure of the protein to the point that it is no longer recognized buy its counter-receptor.

Identification of the significant protein regions involved in binding permits more accurate and efficient screening of putative modulators of binding activity. The invention contemplates of a high throughput screening assay to analyze large libraries of small molecules or peptides, as well as antibodies immunospecific for either or both binding partners, for the ability to modulate interactions of $\beta_2$, $\beta_7$, $\beta_1$, and/or $\beta_3$ integrins with IRPs as well as for the ability to modulate interactions of IRPs with other interacting proteins. While two hybrid screening, scintillation proximity assays (SPA) and immunological methodologies [for example, enzyme-linked immunosorbent assays (ELISA)] disclosed herein are not HTS methods, per se, they are amenable to test many of the compounds listed for an ability to modulate binding. SPA and ELISA are particularly useful in this identification process and can be modified to permit high throughput screening of the test compounds described.

While the present invention has been described in terms of specific embodiments, it is understood that variations and modifications will occur to those skilled in the art. Accordingly, only such limitations as appear in the claims should be placed on the invention.

What is claimed is:

1. A method for identifying a compound that modulates binding between integrin regulatory protein IRP-1 and a β integrin subunit comprising the steps of:

a) contacting IRP-1 or a fragment thereof that binds a β integrin subunit, with a β integrin subunit or a fragment thereof that binds IRP-1;

b) measuring binding between said IRP-1 or fragment thereof, and said β integrin subunit or fragment thereof;

c) measuring binding between said IRP-1 or fragment thereof, and said β integrin subunit or fragment thereof in the presence of a test compound, and d) comparing the measurement in step (b) to the measurement in step (c) wherein a decrease in binding in step (c) indicates the test compound in an inhibitor of binding, and an increase in binding in step (c) indicates the test compound is an activator of binding, wherein said IRP-1 protein is an IRP polypeptide characterized by the ability to abrogate $\alpha_4\beta_7$ binding to VCAM-1 in transfected JY cells and is encoded by a DNA molecule selected from the group consisting of:

a) the human IRP-1 DNA set out in SEQ ID NO: 1; and b) a DNA molecule which hybridizes under stringent conditions to a polynucleotide complementary to the protein coding portion of (a), said stringent conditions including a final wash at 65° C. in 0.2×SSC.

2. A method for identifying a compound that modulates binding between integrin regulatory protein IRP-2 and a β integrin subunit comprising the steps of:

a) contacting IRP-2 or a fragment thereof that binds a β integrin subunit, with a β integrin subunit or a fragment thereof that binds IRP-2;

b) measuring binding between said IRP-2 or fragment thereof, and said β integrin subunit or fragment thereof;

c) measuring binding between said IRP-2 or fragment thereof, and said β integrin subunit or fragment thereof in the presence of a test compound, and d) comparing the measurement in step (b) to the measurement in step (c) wherein a decrease in binding in step (c) indicates the test compound in an inhibitor of binding, and an increase in binding in step (c) indicates the test compound is in activator of binding, wherein said IRP-2 protein is an IRP polypeptide characterized by the ability to abrogate $\alpha_4\beta_7$ binding to VCAM-1 in transfected JY cells and is encoded by a DNA selected from the group consisting of:

a) the human IRP-2 DNA set out in SEQ ID NO: 3; and b) a DNA molecule which hybridizes under stringent conditions to a polynucleotide complementary to the protein coding portion of (a), said stringent conditions including a final wash at 65° C. in 0.2×SSC.

3. A method for identifying a compound that modulates binding between integrin regulatory protein IRP-1 and ADP ribosylation factor (ARF) comprising the steps of:

a) contacting IRP-1 or a fragment thereof that binds ARF, with ARF or a fragment thereof that binds IRP-1;

b) measuring binding between said IRP-1 or fragment thereof, and said ARF or fragment thereof;

c) measuring binding between said IRP-1 or fragment thereof, and said ARF or fragment thereof in the presence of a test compound, and d) comparing the measurement in step (b) to the measurement in step (c) wherein a decrease in binding in step (c) indicates the test compound is an inhibitor of binding, and an increase in binding in step (c) indicates the test compound is an activator of binding, wherein said IRP-1 protein is an IRP polypeptide characterized by the ability to abrogate $\alpha_4\beta_7$ binding to VCAM-1 in transfected JY cells and is encoded by a DNA molecule selected from the group consisting of:

a) the human IRP-1 DNA set out in SEQ ID NO: 1; and b) a DNA molecule which hybridizes under stringent conditions to a polynucleotide complementary to the protein coding portion of (a), said stringent conditions including a final wash at 65° C. in 0.2×SSC.

4. A method for identifying a compound that modulates binding between integrin regulatory protein IRP-2 and ADP ribosylation factor (ARF) comprising the steps of:

a) contacting IRP-2 or a fragment thereof that binds ARF, with ARF or a fragment thereof that binds IRP-2;

b) measuring binding between said IRP-2 or fragment thereof, and said ARF or fragment thereof;

c) measuring binding between said IRP-2 or fragment thereof, and said ARF or fragment thereof in the presence of a test compound, and d) comparing the measurement in step (b) to the measurement in step (c) wherein a decrease in binding in step (c) indicates the test compound is an inhibitor of binding, and an increase in binding in step (c) indicates the test compound is an activator of binding, wherein said IRP-2 protein is an integrin regulatory protein (IRP) polypeptide characterized by the ability to abrogate $\alpha_4\beta_7$ binding to VCAM-1 in transfected JY cells and is encoded by a DNA selected from the group consisting of:

a) the human IRP-2 DNA set out in SEQ ID NO: 3; and b) a DNA molecule which hybridizes under stringent conditions to a polynucleotide complementary to the protein coding portion of (a), said stringent conditions including a final wash at 65° C. in 0.2×SSC.

5. A method for identifying a compound that modulates binding between integrin regulatory protein IRP-1 and phosphatidyl inositol (PI) comprising the steps of:
  a) contacting IRP-1 or a fragment thereof that binds PI, with PI;
  b) measuring binding between said IRP-1 or fragment thereof, and PI;
  c) measuring binding between said IRP-1 or fragment thereof, and PI in the presence of a test compound, and
  d) comparing the measurement in step (b) to the measurement in step (c) wherein a decrease in binding in step (c) indicates the test compound is an inhibitor of binding, and an increase in binding in step (c) indicates the test compound is an activator of binding,
wherein said IRP-1 protein is an integrin regulatory protein (IRP) polypeptide characterized by the ability to abrogate $\alpha_4\beta_7$ binding to VCAM-1 in transfected JY cells and is encoded aby a DNA molecule selected from the group consisting of:
  a) the human IRP-1 DNA set out in SEQ ID NO: 1; and
  b) a DNA molecule which hybridizes under stringent conditions to a polynucleotide complementary to the protein coding portion of (a), said stringent conditions including a final wash at 65° C. in 0.2×SSC.

6. A method for identifying a compound that modulates binding between integrin regulatory protein IRP-2 and phosphatidyl inositol (PI) comprising the steps of:
  a) contacting IRP-2 or a fragment thereof that binds PI, with PI;
  b) measuring binding between said IRP-2 or fragment thereof, and PI;
  c) measuring binding between said IRP-2 or fragment thereof, and PI in the presence of a test compound, and
  d) comparing the measurement in step (b) to the measurement in step (c) wherein a decrease in binding in step (c) indicates the test compound is an inhibitor of binding, and an increase in binding in step (c) indicates the test compound is an activator of binding,
wherein said IRP-2 protein is an integrin regulatory protein (IRP) polypeptide characterized by the ability to abrogate $\alpha_4\beta_7$ binding to VCAM-1 in transfected JY cells and is encoded by a DNA selected from the group consisting of:
  a) the human IRP-2 DNA set out in SEQ ID NO: 3; and
  b) a DNA molecule which hybridizes under stringent conditions to a polynucleotide complementary to the protein coding portion of (a), said stringent conditions including a final wash at 65° C. in 0.2×SSC.

\* \* \* \* \*

UNITED STATES PATENT AND TRADEMARK OFFICE
CERTIFICATE OF CORRECTION

PATENT NO. : 5,958,705
DATED : September 28, 1999
INVENTOR(S) : Staunton et al.

It is certified that error appears in the above-identified patent and that said Letters Patent is hereby corrected as shown below:

Title page, References Cited,
Item [56], U.S. PATENT DOCUMENTS, "5, 587,166  12/1995 Donachie" should be -- 5,587,166  12/1996 Donachie --.

Column 1,
Van der Vieren et al., "Perferentially" should be -- Preferentially --.
"Bowman, et al." should be -- Boman et al. --.

References Cited, OTHER PUBLICATIONS,
Column 2,
Miyamoto et al., "267:883-835" should be -- 267:883-885 --
Schiller and Kolanus, "Itegrin" should be -- Integrin --.
Shevell et al., "EMBO3O" should be -- EMB3O --.
Mahadevan, et al., "$\alpha$ARK1" should be -- $\beta$ARK1 --.
"Morla, er al." should be -- Morla et al. --.

Column 2,
Line 35, "75-58" should be -- 75-78 --.
Line 60, after "conditions" insert -- . --

Column 3,
Line 14, "3" should be -- 2 --.

Column 9,
Line 61, "a" should be -- an --.

Column 10,
Line 55, "a" should be -- an --.

Column 13,
Line 65, "an" should be -- a --.

Column 16,
Line 36, "phophatidylcholine" should be -- phosphatidycholine --.

Column 18,
Line 13, "lmunoblotting" should be -- lmmunoblotting --.

UNITED STATES PATENT AND TRADEMARK OFFICE
CERTIFICATE OF CORRECTION

PATENT NO. : 5,958,705
DATED : September 28, 1999
INVENTOR(S) : Staunton et al.

It is certified that error appears in the above-identified patent and that said Letters Patent is hereby corrected as shown below:

Column 20,
Line 49, "1.5 dynes/cM$^2$" should be -- 1.5 dynes/cm$^2$ --.

Column 21,
Line 32, "the" should be -- then --.

Column 22,
Line 66, "GFB-B2-1" should be -- GFP-B2-1 --.

Column 23,
Line 64, "Cheomotaxis" should be -- Chemotaxis --.

Column 27,
Line 1, "present" should be -- presence --.

Column 30,
Line 7, "buy" should be -- by --.

Column 55,
Line 60, "in" should be -- an --.

Column 57,
Line 19, "aby" should be -- by --.

Signed and Sealed this

Sixteenth Day of October, 2001

Attest:

NICHOLAS P. GODICI
Attesting Officer   Acting Director of the United States Patent and Trademark Office

SEQUENCE LISTING (1) GENERAL INFORMATION:

(iii) NUMBER OF SEQUENCES: 32

(2) INFORMATION FOR SEQ ID NO:1:

(i) SEQUENCE CHARACTERISTICS:
        (A) LENGTH: 1700 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: CDS
        (B) LOCATION: 283..1482

(xi) SEQUENCE DESCRIPTION: SEQ ID NO:1:

```
TCCTAGATGA TCTCGAGAGG CGCAGTGTGC TCTAAAGGCG AGGGCGGTGA GGACGACAGC      60

GCCCACTGTG GATTGGACAG TGTCAAAAAG AGGGGCGGTC CCTACTGAAG GGGCGGTTGG     120

GCGACGAAGG GAAGAGTCTT TTCAGCGCTG AGGACTGGCG CTGAGGAGGC GGCGGTGGCT     180

CCCGGGGCGT TTGAGCGGGC TCACCCGAGC CCGCGGGCCA ACGCGGATCC AGGCCCGACT     240

GGCGGGACCG CCCCGGATTC CCCGCGGGCC TTCCTAGCCG CC ATG GAG GAC GGC        294
                                                 Met Glu Asp Gly
                                                   1

GTC TAT GAA CCC CCA GAC CTG ACT CCG GAG GAG CGG ATG GAG CTG GAG       342
Val Tyr Glu Pro Pro Asp Leu Thr Pro Glu Glu Arg Met Glu Leu Glu
  5                  10                  15                  20

AAC ATC CGG CGG CGG AAG CAG GAG CTG CTG GTG GAG ATT CAG CGC CTG       390
Asn Ile Arg Arg Arg Lys Gln Glu Leu Leu Val Glu Ile Gln Arg Leu
```

|  |  |  |  |  |  |  |  |  |  |  |  |  |  |  |  |
|---|---|---|---|---|---|---|---|---|---|---|---|---|---|---|---|
|  |  |  |  | 25 |  |  |  | 30 |  |  |  | 35 |  |  |  |
| CGG | GAG | GAG | CTC | AGT | GAA | GCC | ATG | AGC | GAG | GTG | GAG | GGG | CTG | GAG | GCC | 438 |
| Arg | Glu | Glu | Leu | Ser | Glu | Ala | Met | Ser | Glu | Val | Glu | Gly | Leu | Glu | Ala |  |
|  |  |  | 40 |  |  |  | 45 |  |  |  | 50 |  |  |  |  |  |
| AAT | GAG | GGC | AGT | AAG | ACC | TTG | CAA | CGG | AAC | CGG | AAG | ATG | GCA | ATG | GGC | 486 |
| Asn | Glu | Gly | Ser | Lys | Thr | Leu | Gln | Arg | Asn | Arg | Lys | Met | Ala | Met | Gly |  |
|  |  | 55 |  |  |  | 60 |  |  |  | 65 |  |  |  |  |  |  |
| AGG | AAG | AAG | TTC | AAC | ATG | GAC | CCC | AAG | AAG | GGG | ATC | CAG | TTC | TTG | GTG | 534 |
| Arg | Lys | Lys | Phe | Asn | Met | Asp | Pro | Lys | Lys | Gly | Ile | Gln | Phe | Leu | Val |  |
|  | 70 |  |  |  | 75 |  |  |  | 80 |  |  |  |  |  |  |  |
| GAG | AAT | GAA | CTG | CTG | CAG | AAC | ACA | CCC | GAG | GAG | ATC | GCC | CGC | TTC | CTG | 582 |
| Glu | Asn | Glu | Leu | Leu | Gln | Asn | Thr | Pro | Glu | Glu | Ile | Ala | Arg | Phe | Leu |  |
| 85 |  |  |  | 90 |  |  |  | 95 |  |  |  | 100 |  |  |  |  |
| TAC | AAG | GGC | GAG | GGG | CTG | AAC | AAG | ACA | GCC | ATC | GGG | GAC | TAC | CTG | GGG | 630 |
| Tyr | Lys | Gly | Glu | Gly | Leu | Asn | Lys | Thr | Ala | Ile | Gly | Asp | Tyr | Leu | Gly |  |
|  |  |  | 105 |  |  |  | 110 |  |  |  | 115 |  |  |  |  |  |
| GAG | AGG | GAA | GAA | CTG | AAC | CTG | GCA | GTG | CTC | CAT | GCT | TTT | GTG | GAT | CTG | 678 |
| Glu | Arg | Glu | Glu | Leu | Asn | Leu | Ala | Val | Leu | His | Ala | Phe | Val | Asp | Leu |  |
|  |  | 120 |  |  |  | 125 |  |  |  | 130 |  |  |  |  |  |  |
| CAT | GAG | TTC | ACC | GAC | CTC | AAT | CTG | GTG | CAG | GCC | CTC | AGG | CAG | TTT | CTA | 726 |
| His | Glu | Phe | Thr | Asp | Leu | Asn | Leu | Val | Gln | Ala | Leu | Arg | Gln | Phe | Leu |  |
|  | 135 |  |  |  | 140 |  |  |  | 145 |  |  |  |  |  |  |  |
| TGG | AGC | TTT | CGC | CTA | CCC | GGA | GAG | GCC | CAG | AAA | ATT | GAC | CGG | ATG | ATG | 774 |
| Trp | Ser | Phe | Arg | Leu | Pro | Gly | Glu | Ala | Gln | Lys | Ile | Asp | Arg | Met | Met |  |
| 150 |  |  |  | 155 |  |  |  | 160 |  |  |  |  |  |  |  |  |
| GAG | GCC | TTC | GCC | CAG | CGA | TAC | TGC | CTG | TGC | AAC | CCT | GGG | GTT | TTC | CAG | 822 |
| Glu | Ala | Phe | Ala | Gln | Arg | Tyr | Cys | Leu | Cys | Asn | Pro | Gly | Val | Phe | Gln |  |
| 165 |  |  |  | 170 |  |  |  | 175 |  |  |  | 180 |  |  |  |  |
| TCC | ACA | GAC | ACG | TGC | TAT | GTG | CTG | TCC | TTC | GCC | GTC | ATC | ATG | CTC | AAC | 870 |
| Ser | Thr | Asp | Thr | Cys | Tyr | Val | Leu | Ser | Phe | Ala | Val | Ile | Met | Leu | Asn |  |
|  |  |  | 185 |  |  |  | 190 |  |  |  | 195 |  |  |  |  |  |
| ACC | AGT | CTC | CAC | AAT | CCC | AAT | GTC | CGG | GAC | AAG | CCG | GGC | CTG | GAG | CGC | 918 |
| Thr | Ser | Leu | His | Asn | Pro | Asn | Val | Arg | Asp | Lys | Pro | Gly | Leu | Glu | Arg |  |
|  |  | 200 |  |  |  | 205 |  |  |  | 210 |  |  |  |  |  |  |
| TTT | GTG | GCC | ATG | AAC | CGG | GGC | ATC | AAC | GAG | GGC | GGG | GAC | CTG | CCT | GAG | 966 |
| Phe | Val | Ala | Met | Asn | Arg | Gly | Ile | Asn | Glu | Gly | Gly | Asp | Leu | Pro | Glu |  |
|  | 215 |  |  |  | 220 |  |  |  | 225 |  |  |  |  |  |  |  |
| GAG | CTG | CTC | AGG | AAC | CTG | TAC | GAC | AGC | ATC | CGA | AAT | GAG | CCC | TTC | AAG | 1014 |
| Glu | Leu | Leu | Arg | Asn | Leu | Tyr | Asp | Ser | Ile | Arg | Asn | Glu | Pro | Phe | Lys |  |
| 230 |  |  |  | 235 |  |  |  | 240 |  |  |  |  |  |  |  |  |
| ATT | CCT | GAG | GAT | GAC | GGG | AAT | GAC | CTG | ACC | CAC | ACC | TTC | TTC | AAC | CCG | 1062 |
| Ile | Pro | Glu | Asp | Asp | Gly | Asn | Asp | Leu | Thr | His | Thr | Phe | Phe | Asn | Pro |  |
| 245 |  |  |  | 250 |  |  |  | 255 |  |  |  | 260 |  |  |  |  |
| GAC | CGG | GAG | GGC | TGG | CTC | CTG | AAG | CTG | GGG | GGC | CGG | GTG | AAG | ACG | TGG | 1110 |
| Asp | Arg | Glu | Gly | Trp | Leu | Leu | Lys | Leu | Gly | Gly | Arg | Val | Lys | Thr | Trp |  |
|  |  |  | 265 |  |  |  | 270 |  |  |  | 275 |  |  |  |  |  |
| AAG | CGG | CGC | TGG | TTT | ATC | CTC | ACA | GAC | AAC | TGC | CTC | TAC | TAC | TTT | GAG | 1158 |
| Lys | Arg | Arg | Trp | Phe | Ile | Leu | Thr | Asp | Asn | Cys | Leu | Tyr | Tyr | Phe | Glu |  |
|  |  | 280 |  |  |  | 285 |  |  |  | 290 |  |  |  |  |  |  |
| TAC | ACC | ACG | GAC | AAG | GAG | CCC | CGA | GGA | ATC | ATC | CCC | CTG | GAG | AAT | CTG | 1206 |
| Tyr | Thr | Thr | Asp | Lys | Glu | Pro | Arg | Gly | Ile | Ile | Pro | Leu | Glu | Asn | Leu |  |
|  | 295 |  |  |  | 300 |  |  |  | 305 |  |  |  |  |  |  |  |
| AGC | ATC | CGA | GAG | GTG | GAC | GAC | CCC | CGG | AAA | CCG | AAC | TGC | TTT | GAA | CTT | 1254 |
| Ser | Ile | Arg | Glu | Val | Asp | Asp | Pro | Arg | Lys | Pro | Asn | Cys | Phe | Glu | Leu |  |
| 310 |  |  |  | 315 |  |  |  | 320 |  |  |  |  |  |  |  |  |
| TAC | ATC | CCC | AAC | AAC | AAG | GGG | CAG | CTC | ATC | AAA | GCC | TGC | AAA | ACT | GAG | 1302 |
| Tyr | Ile | Pro | Asn | Asn | Lys | Gly | Gln | Leu | Ile | Lys | Ala | Cys | Lys | Thr | Glu |  |
| 325 |  |  |  | 330 |  |  |  | 335 |  |  |  | 340 |  |  |  |  |
| GCG | GAC | GGC | CGA | GTG | GTG | GAG | GGA | AAC | CAC | ATG | GTG | TAC | CGG | ATC | TCG | 1350 |
| Ala | Asp | Gly | Arg | Val | Val | Glu | Gly | Asn | His | Met | Val | Tyr | Arg | Ile | Ser |  |

```
                    345                 350                 355
GCC CCC ACG CAG GAG GAG AAG GAC GAG TGG ATC AAG TCC ATC CAG GCG    1398
Ala Pro Thr Gln Glu Glu Lys Asp Glu Trp Ile Lys Ser Ile Gln Ala
        360                 365                 370

GCT GTG AGT GTG GAC CCC TTC TAT GAG ATG CTG GCA GCG AGA AAG AAG    1446
Ala Val Ser Val Asp Pro Phe Tyr Glu Met Leu Ala Ala Arg Lys Lys
        375                 380                 385

CGG ATT TCA GTC AAG AAG AAG CAG GAG CAG CCC TGA CCCCCTGCCC         1492
Arg Ile Ser Val Lys Lys Lys Gln Glu Gln Pro
        390                 395

CCAACTCCAT TATTTATTAC GGAGCTGCCC CGCCTGGGTG GCCGGACCCC TGGGCCTTGG  1552

GGCTGTGGAT CCTGGTTCCC TGTTTGGAAA ATTCACCACC TCTAGCTCCT CACTGTTCTT  1612

TGTAATTAAC ACGCTGTTGG TAACTTTAGA GCACACTGGC GCCCGTTACT AGTGGATCCG  1672

AGCTCGGTAC CAAGCGTGGT CTCCCTAT                                    1700
```

(2) INFORMATION FOR SEQ ID NO:2:

(i) SEQUENCE CHARACTERISTICS:
        (A) LENGTH: 399 amino acids
        (B) TYPE: amino acid
        (D) TOPOLOGY: linear (ii) MOLECULE TYPE: protein (xi) SEQUENCE DESCRIPTION: SEQ ID NO:2:

```
Met Glu Asp Gly Val Tyr Glu Pro Pro Asp Leu Thr Pro Glu Arg
 1               5                  10                  15

Met Glu Leu Glu Asn Ile Arg Arg Lys Gln Glu Leu Leu Val Glu
                20                  25                  30

Ile Gln Arg Leu Arg Glu Glu Leu Ser Glu Ala Met Ser Glu Val Glu
            35                  40                  45

Gly Leu Glu Ala Asn Glu Gly Ser Lys Thr Leu Gln Arg Asn Arg Lys
    50                  55                  60

Met Ala Met Gly Arg Lys Lys Phe Asn Met Asp Pro Lys Lys Gly Ile
65                  70                  75                  80

Gln Phe Leu Val Glu Asn Glu Leu Leu Gln Asn Thr Pro Glu Glu Ile
                85                  90                  95

Ala Arg Phe Leu Tyr Lys Gly Glu Gly Leu Asn Lys Thr Ala Ile Gly
            100                 105                 110

Asp Tyr Leu Gly Glu Arg Glu Glu Leu Asn Leu Ala Val Leu His Ala
        115                 120                 125

Phe Val Asp Leu His Glu Phe Thr Asp Leu Asn Leu Val Gln Ala Leu
    130                 135                 140

Arg Gln Phe Leu Trp Ser Phe Arg Leu Pro Gly Glu Ala Gln Lys Ile
145                 150                 155                 160

Asp Arg Met Met Glu Ala Phe Ala Gln Arg Tyr Cys Leu Cys Asn Pro
                165                 170                 175

Gly Val Phe Gln Ser Thr Asp Thr Cys Tyr Val Leu Ser Phe Ala Val
            180                 185                 190

Ile Met Leu Asn Thr Ser Leu His Asn Pro Asn Val Arg Asp Lys Pro
        195                 200                 205

Gly Leu Glu Arg Phe Val Ala Met Asn Arg Gly Ile Asn Glu Gly Gly
    210                 215                 220

Asp Leu Pro Glu Glu Leu Leu Arg Asn Leu Tyr Asp Ser Ile Arg Asn
225                 230                 235                 240

Glu Pro Phe Lys Ile Pro Glu Asp Asp Gly Asn Asp Leu Thr His Thr
```

```
                    245                 250                 255
Phe Phe Asn Pro Asp Arg Glu Gly Trp Leu Leu Lys Leu Gly Gly Arg
            260                 265                 270

Val Lys Thr Trp Lys Arg Arg Trp Phe Ile Leu Thr Asp Asn Cys Leu
        275                 280                 285

Tyr Tyr Phe Glu Tyr Thr Thr Asp Lys Glu Pro Arg Gly Ile Ile Pro
    290                 295                 300

Leu Glu Asn Leu Ser Ile Arg Glu Val Asp Asp Pro Arg Lys Pro Asn
305                 310                 315                 320

Cys Phe Glu Leu Tyr Ile Pro Asn Asn Lys Gly Gln Leu Ile Lys Ala
                325                 330                 335

Cys Lys Thr Glu Ala Asp Gly Arg Val Val Glu Gly Asn His Met Val
            340                 345                 350

Tyr Arg Ile Ser Ala Pro Thr Gln Glu Glu Lys Asp Glu Trp Ile Lys
        355                 360                 365

Ser Ile Gln Ala Ala Val Ser Val Asp Pro Phe Tyr Glu Met Leu Ala
    370                 375                 380

Ala Arg Lys Lys Arg Ile Ser Val Lys Lys Lys Gln Glu Gln Pro
385                 390                 395
```

(2) INFORMATION FOR SEQ ID NO:3:

(i) SEQUENCE CHARACTERISTICS:
        (A) LENGTH: 1260 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: CDS
        (B) LOCATION: 70..1254

(xi) SEQUENCE DESCRIPTION: SEQ ID NO:3:

```
CGGCCGCCAG TGTGCTCTAA AGCAGCAAGC GACAGGAGCA CGGGTCATCT TTTCCCCAGA      60

GGCGTCGGA ATG GAC CTG TGC CAC CCA GAG CCC GCG GAG CTG AGC AGC         108
          Met Asp Leu Cys His Pro Glu Pro Ala Glu Leu Ser Ser
              Met Asp Leu Cys His Pro Glu Pro Ala Glu Leu Ser Ser
                                405                 410

GGG GAG ACG GAA GAG TTA CAG AGG ATC AAG TGG CAC CGA AAG CAG CTC       156
Gly Glu Thr Glu Glu Leu Gln Arg Ile Lys Trp His Arg Lys Gln Leu
415                 420                 425

CTG GAG GAC ATC CAG AAG CTG AAG GAT GAG ATT GCA GAT GTG TTT GCC       204
Leu Glu Asp Ile Gln Lys Leu Lys Asp Glu Ile Ala Asp Val Phe Ala
430                 435                 440                 445

CAA ATC GAC TGC TTC GAG AGT GCG GAG GAG AGC CGG ATG GCC CAG AAG       252
Gln Ile Asp Cys Phe Glu Ser Ala Glu Glu Ser Arg Met Ala Gln Lys
            450                 455                 460

GAG AAG GAG CTG TGT ATT GGG CGC AAG AAG TTC AAC ATG GAC CCC GCC       300
Glu Lys Glu Leu Cys Ile Gly Arg Lys Lys Phe Asn Met Asp Pro Ala
        465                 470                 475

AAG GGT ATC CAG TAT TTC ATT GAG CAC AAG CTG CTG TCC CCT GAC GTC       348
Lys Gly Ile Gln Tyr Phe Ile Glu His Lys Leu Leu Ser Pro Asp Val
    480                 485                 490

CAG GAC ATT GCA CGG TTC CTG TAT AAA GGC GAG GGC CTC AAC AAG ACA       396
Gln Asp Ile Ala Arg Phe Leu Tyr Lys Gly Glu Gly Leu Asn Lys Thr
495                 500                 505

GCC ATT GGT ACC TAC CTG GGG GAG AGG GAT CCC ATC AAC CTG CAG GTC       444
Ala Ile Gly Thr Tyr Leu Gly Glu Arg Asp Pro Ile Asn Leu Gln Val
510                 515                 520                 525
```

```
CTC CAG GCC TTC GTG GAC TGC CAC GAG TTC GCC AAC CTC AAC CTC GTC         492
Leu Gln Ala Phe Val Asp Cys His Glu Phe Ala Asn Leu Asn Leu Val
            530                 535                 540

CAG GCC CTC AGG CAG TTC CTG TGG AGC TTC CGG CTG CCG GGC GAG GCC         540
Gln Ala Leu Arg Gln Phe Leu Trp Ser Phe Arg Leu Pro Gly Glu Ala
            545                 550                 555

CAG AAG ATA GAC CGG ATG ATG GAG GCC TTT GCC ACT CGA TAC TGC CTC         588
Gln Lys Ile Asp Arg Met Met Glu Ala Phe Ala Thr Arg Tyr Cys Leu
            560                 565                 570

TGC AAC CCA GGC GTC TTC CAG TCC ACA GAC ACC TGC TAC GTG TTG TCC         636
Cys Asn Pro Gly Val Phe Gln Ser Thr Asp Thr Cys Tyr Val Leu Ser
575                 580                 585

TTC TCC ATC ATC ATG CTC AAC ACC AGC CTC CAC AAT CCC AAC GTC CGG         684
Phe Ser Ile Ile Met Leu Asn Thr Ser Leu His Asn Pro Asn Val Arg
590                 595                 600                 605

GAC AGG CCG CCT TTT GAG CGC TTT GTG TCC ATG AAC CGC GGC ATC AAC         732
Asp Arg Pro Pro Phe Glu Arg Phe Val Ser Met Asn Arg Gly Ile Asn
                610                 615                 620

AAT GGT AGC GAC CTG CCC GAG GAC CAG CTG CGG AAC CTC TTC GAC AGC         780
Asn Gly Ser Asp Leu Pro Glu Asp Gln Leu Arg Asn Leu Phe Asp Ser
            625                 630                 635

ATC AAG AGT GAG CCA TTC TCC ATC CCT GAG GAC GAC GGC AAT GAC CTC         828
Ile Lys Ser Glu Pro Phe Ser Ile Pro Glu Asp Asp Gly Asn Asp Leu
            640                 645                 650

ACT CAC ACC TTC TTC AAT CCA GAC CGG GAG GGT TGG CTG CTC AAG CTA         876
Thr His Thr Phe Phe Asn Pro Asp Arg Glu Gly Trp Leu Leu Lys Leu
            655                 660                 665

GGG GGC CGC GTG AAG ACG TGG AAA CGG CGC TGG TTC ATC CTG ACC GAC         924
Gly Gly Arg Val Lys Thr Trp Lys Arg Arg Trp Phe Ile Leu Thr Asp
670                 675                 680                 685

AAC TGC CTC TAC TAC TTC GAG TTC ACC ACT GAC AAG GAG CCA CGG GGA         972
Asn Cys Leu Tyr Tyr Phe Glu Phe Thr Thr Asp Lys Glu Pro Arg Gly
            690                 695                 700

ATT ATA CCT CTT GAG AAC CTC TCG GTG CAG AAG GTG GAT GAC CCC AAG        1020
Ile Ile Pro Leu Glu Asn Leu Ser Val Gln Lys Val Asp Asp Pro Lys
            705                 710                 715

AAG CCA TTC TGC CTG GAG CTC TAC AAC CCT AGC TGC CGA GGC CAG AAA        1068
Lys Pro Phe Cys Leu Glu Leu Tyr Asn Pro Ser Cys Arg Gly Gln Lys
            720                 725                 730

ATC AAG GCC TGC AAG ACC GAT GGC GAC GGC AGG GTG GTG GAG GGC AAG        1116
Ile Lys Ala Cys Lys Thr Asp Gly Asp Gly Arg Val Val Glu Gly Lys
735                 740                 745

CAC GAA TCG TAC CGC ATC TCA GCC ACC AGT GCC GAG GAA CGT GAC CAG        1164
His Glu Ser Tyr Arg Ile Ser Ala Thr Ser Ala Glu Glu Arg Asp Gln
750                 755                 760                 765

TGG ATC GAG TCC ATC CGA GCC AGC ATC ACC CGT GTC CCC TTC TAC GAC        1212
Trp Ile Glu Ser Ile Arg Ala Ser Ile Thr Arg Val Pro Phe Tyr Asp
            770                 775                 780

CTG GTC TCT ACT CGG AAG AAG AAG ATT GCC AGC AAG CAG TGA               1254
Leu Val Ser Thr Arg Lys Lys Lys Ile Ala Ser Lys Gln
            785                 790

GATTCC                                                                 1260

(2) INFORMATION FOR SEQ ID NO:4:

(i) SEQUENCE CHARACTERISTICS:
        (A) LENGTH: 394 amino acids
        (B) TYPE: amino acid
        (D) TOPOLOGY: linear (ii) MOLECULE TYPE: protein
```

(xi) SEQUENCE DESCRIPTION: SEQ ID NO:4:

```
Met Asp Leu Cys His Pro Glu Pro Ala Glu Leu Ser Ser Gly Glu Thr
 1               5                  10                  15

Glu Glu Leu Gln Arg Ile Lys Trp His Arg Lys Gln Leu Leu Glu Asp
            20                  25                  30

Ile Gln Lys Leu Lys Asp Glu Ile Ala Asp Val Phe Ala Gln Ile Asp
            35                  40                  45

Cys Phe Glu Ser Ala Glu Ser Arg Met Ala Gln Lys Glu Lys Glu
        50                  55                  60

Leu Cys Ile Gly Arg Lys Lys Phe Asn Met Asp Pro Ala Lys Gly Ile
65                  70                  75                  80

Gln Tyr Phe Ile Glu His Lys Leu Leu Ser Pro Asp Val Gln Asp Ile
                85                  90                  95

Ala Arg Phe Leu Tyr Lys Gly Glu Gly Leu Asn Lys Thr Ala Ile Gly
                100                 105                 110

Thr Tyr Leu Gly Glu Arg Asp Pro Ile Asn Leu Gln Val Leu Gln Ala
            115                 120                 125

Phe Val Asp Cys His Glu Phe Ala Asn Leu Asn Leu Val Gln Ala Leu
        130                 135                 140

Arg Gln Phe Leu Trp Ser Phe Arg Leu Pro Gly Glu Ala Gln Lys Ile
145                 150                 155                 160

Asp Arg Met Met Glu Ala Phe Ala Thr Arg Tyr Cys Leu Cys Asn Pro
                165                 170                 175

Gly Val Phe Gln Ser Thr Asp Thr Cys Tyr Val Leu Ser Phe Ser Ile
                180                 185                 190

Ile Met Leu Asn Thr Ser Leu His Asn Pro Asn Val Arg Asp Arg Pro
        195                 200                 205

Pro Phe Glu Arg Phe Val Ser Met Asn Arg Gly Ile Asn Asn Gly Ser
    210                 215                 220

Asp Leu Pro Glu Asp Gln Leu Arg Asn Leu Phe Asp Ser Ile Lys Ser
225                 230                 235                 240

Glu Pro Phe Ser Ile Pro Glu Asp Asp Gly Asn Asp Leu Thr His Thr
                245                 250                 255

Phe Phe Asn Pro Asp Arg Glu Gly Trp Leu Leu Lys Leu Gly Gly Arg
            260                 265                 270

Val Lys Thr Trp Lys Arg Arg Trp Phe Ile Leu Thr Asp Asn Cys Leu
        275                 280                 285

Tyr Tyr Phe Glu Phe Thr Thr Asp Lys Glu Pro Arg Gly Ile Ile Pro
    290                 295                 300

Leu Glu Asn Leu Ser Val Gln Lys Val Asp Asp Pro Lys Lys Pro Phe
305                 310                 315                 320

Cys Leu Glu Leu Tyr Asn Pro Ser Cys Arg Gly Gln Lys Ile Lys Ala
                325                 330                 335

Cys Lys Thr Asp Gly Asp Gly Arg Val Val Glu Gly Lys His Glu Ser
            340                 345                 350

Tyr Arg Ile Ser Ala Thr Ser Ala Glu Glu Arg Asp Gln Trp Ile Glu
        355                 360                 365

Ser Ile Arg Ala Ser Ile Thr Arg Val Pro Phe Tyr Asp Leu Val Ser
    370                 375                 380

Thr Arg Lys Lys Lys Ile Ala Ser Lys Gln
385                 390
```

(2) INFORMATION FOR SEQ ID NO:5:

(i) SEQUENCE CHARACTERISTICS:
            (A) LENGTH: 29 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:5:

ATATACGCGT ACCTTCTTCA ACCCGGACC                                              29

(2) INFORMATION FOR SEQ ID NO:6:

(i) SEQUENCE CHARACTERISTICS:
            (A) LENGTH: 29 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:6:

ATATGTCGAC TCAGGGCTGC TCCTGCTTC                                              29

(2) INFORMATION FOR SEQ ID NO:7:

(i) SEQUENCE CHARACTERISTICS:
            (A) LENGTH: 28 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:7:

ATATCATATG GAGGAGGACG ACAGCTAC                                               28

(2) INFORMATION FOR SEQ ID NO:8:

(i) SEQUENCE CHARACTERISTICS:
            (A) LENGTH: 29 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:8:

ATATCTCGAG TCAGTGTCGC TTCGTGGAG                                              29

(2) INFORMATION FOR SEQ ID NO:9:

(i) SEQUENCE CHARACTERISTICS:
            (A) LENGTH: 71 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:9:

ATATGCTAGC CACCATGGGG TACCCATACG ATGTTCCTGA CTATGCGACG CGTATGGAGG            60

AGGACGACAG C                                                                71

(2) INFORMATION FOR SEQ ID NO:10:

(i) SEQUENCE CHARACTERISTICS:
            (A) LENGTH: 68 base pairs
            (B) TYPE: nucleic acid (C) STRANDEDNESS: single
            (D) TOPOLOGY: linear (ii) MOLECULE TYPE: DNA (xi) SEQUENCE DESCRIPTION: SEQ ID NO:10:

ATATGTCGAC TCACGCATAG TACAGGAACA TCGTATGGGT ACATACGCGT GTGTCGCTTC          60

GTGGAGGA                                                                  68

(2) INFORMATION FOR SEQ ID NO:11:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:11:

TAATACGACT CACTATAGGG                                                     20

(2) INFORMATION FOR SEQ ID NO:12:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:12:

ATATACGCGT ACTTTCTTCA ATCCAGACCG                                          30

(2) INFORMATION FOR SEQ ID NO:13:

(i) SEQUENCE CHARACTERISTICS:
            (A) LENGTH: 29 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:13:

ATATTCTAGA TCAGTGTCGC TTCGTGGAG                                           29

(2) INFORMATION FOR SEQ ID NO:14:

(i) SEQUENCE CHARACTERISTICS:
            (A) LENGTH: 29 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:14:

ATATACGCGT ATGGAGGACG GCGTCTATG                                           29

(2) INFORMATION FOR SEQ ID NO:15:

(i) SEQUENCE CHARACTERISTICS:
            (A) LENGTH: 33 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:15:

ATATGAATTC CACCATGGAC CTGTGCCACC CAG            33

(2) INFORMATION FOR SEQ ID NO:16:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:16:

ATATGTCGAC TCACTGCTTG CTGGCAATC            29

(2) INFORMATION FOR SEQ ID NO:17:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:17:

ATATACGCGT ACCTTCTTCA ATCCAGAC            28

(2) INFORMATION FOR SEQ ID NO:18:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:18:

ATATGTCGAC TCACTGCTTG CTGGCAATC            29

(2) INFORMATION FOR SEQ ID NO:19:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:19:

ATATACGCGT ATGGACCTGT GCCACCCAG            29

(2) INFORMATION FOR SEQ ID NO:20:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:20:

```
ATATCTCGAG CTATGGAGGA CGGCGTCTAT                                30
```

(2) INFORMATION FOR SEQ ID NO:21:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:21:

```
ATATAAGCTT GCGGCCGCTC AGGGCTGCTC CTGCTTC                        37
```

(2) INFORMATION FOR SEQ ID NO:22:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:22:

```
ATATCTCGAG CTATGGAGGA GGACGACAGC TAC                            33
```

(2) INFORMATION FOR SEQ ID NO:23:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:23:

```
ATATAAGCTT GCGGCCGCTC AGTGTCGCTT CGTGGAGG                       38
```

(2) INFORMATION FOR SEQ ID NO:24:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:24:

```
ATATCTCGAG CTATGGACCT GTGCCACCCA G                              31
```

(2) INFORMATION FOR SEQ ID NO:25:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:25:

```
ATATAAGCTT GCGGCCGCTC ACTGCTTGCT GGCAATCTTC                    40
```

(2) INFORMATION FOR SEQ ID NO:26:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:26:

```
ATATCTCGAG CTATGAGCGA GGTGGAGGGG CTG                           33
```

(2) INFORMATION FOR SEQ ID NO:27:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:27:

```
ATATAAGCTT GCGGCCGCTC AGAAGGTGTG GGTCAGGTC                     39
```

(2) INFORMATION FOR SEQ ID NO:28:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:28:

```
ATATCTCGAG CTATGACCTT CTTCAACCCG G                             31
```

(2) INFORMATION FOR SEQ ID NO:29:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:29:

```
GTCAATTTTC TGGGCCGCTC CGGGTAGGCG AAA                           33
```

(2) INFORMATION FOR SEQ ID NO:30:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:30:

TGTGAGGATA AACCAGGCCC GCTTCCACGT CTTC            34

(2) INFORMATION FOR SEQ ID NO:31:

(i) SEQUENCE CHARACTERISTICS:
        (A) LENGTH: 377 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:31:

```
Met Thr Leu Pro Lys Val Arg Lys Arg Lys Ala Gln Leu Val Asp Glu
 1               5                  10                  15

Ile Glu Ala Leu Lys Asn Glu Val Arg Glu Val Asp Glu Glu Leu Asp
             20                  25                  30

Gln Val Tyr Tyr Thr His Pro Lys Ser Lys Glu Tyr His Lys Ile Val
         35                  40                  45

Val Asn Gly Arg Lys Lys Phe Asn Gln Asp Pro Trp Lys Ala Leu Asp
 50                  55                  60

Trp Leu Ala Ser Arg Asn Val Val Ala Lys Asp Pro Gln Ala Leu Ala
 65                  70                  75                  80

Leu Trp Met Lys Ala Gly Glu Gly Leu Ser Lys Ser Ala Ile Gly Glu
                 85                  90                  95

Ile Leu Gly Asp Asn Arg Pro Phe Ala Leu Glu Thr Leu Asp Arg Phe
            100                 105                 110

Thr Lys Glu His Lys Leu His Asp Val Pro Ile Val Pro Ala Leu Arg
        115                 120                 125

Gln Tyr Leu Phe Ser Phe Arg Leu Pro Gly Glu Ser Gln Lys Ile Asn
    130                 135                 140

Arg Ile Leu Glu Lys Phe Ala Glu Val Tyr Ala Asn Gln Asn Pro Ser
145                 150                 155                 160

Tyr Gly Asn Ala Asp Gln Ala His Thr Val Ala Tyr Ser Cys Ile Met
                165                 170                 175

Val Asn Thr Leu Leu His Asn Pro Asn Val Lys Asp Lys Pro Ser Leu
            180                 185                 190

Glu Lys Tyr Ile Glu Met Asn Glu Gln Leu Leu Glu Lys Gly Ala Ile
        195                 200                 205

Thr Ile Glu Gln Leu Thr Glu Val Tyr Glu Ser Val Ser Val Thr Gln
    210                 215                 220

Phe Lys Ile Pro Asp Glu Val Ser Thr Ser Gly Lys Gly Thr Val Asn
225                 230                 235                 240

Asp Ile Leu Leu His Ala Glu Arg Glu Gly Trp Leu Phe Lys Gln Ser
                245                 250                 255

Ser Asn Pro Leu Phe Ser Gly Ala Leu Ser Trp Lys Lys Arg Trp Phe
            260                 265                 270

Val Leu Ser Glu Asn Cys Leu Tyr Tyr Phe Asp Gln Met Thr Asp Lys
        275                 280                 285

Glu Pro Lys Gly Ile Ile Thr Leu Ala Asn Val Gly Ile Arg Lys Val
    290                 295                 300

Glu Ala Pro Ser Arg Pro Phe Met Phe Glu Ile Phe Ser Leu Ser Asp
305                 310                 315                 320

Gly Gln Ile Lys Ala Cys Lys Thr Glu Gln Asp Gly Arg Leu Val Glu
                325                 330                 335

Gly Arg His Ser Ile Tyr Lys Ile Cys Ala Val Asn Asp Glu Asp Met
            340                 345                 350
```

```
Arg Ser Trp Ile Asn Ala Ile Ser Arg Met Met Ala Pro Gln Gln His
        355                 360                 365

Leu Leu Ala Arg Pro Lys Ser Thr His
        370                 375
```

(2) INFORMATION FOR SEQ ID NO:32:

(i) SEQUENCE CHARACTERISTICS:
        (A) LENGTH: 398 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:32:

```
Met Glu Glu Asp Asp Ser Tyr Val Pro Ser Asp Leu Thr Ala Glu Glu
1               5                   10                  15

Arg Gln Glu Leu Glu Asn Ile Arg Arg Lys Gln Glu Leu Leu Ala
                20                  25                  30

Asp Ile Gln Arg Leu Lys Asp Glu Ile Ala Glu Val Ala Asn Glu Ile
            35                  40                  45

Glu Asn Leu Gly Ser Thr Glu Glu Arg Lys Asn Met Gln Arg Asn Lys
    50                  55                  60

Gln Val Ala Met Gly Arg Lys Lys Phe Asn Met Asp Pro Lys Lys Gly
65                  70                  75                  80

Ile Gln Phe Leu Ile Glu Asn Asp Leu Leu Lys Asn Thr Cys Glu Asp
                85                  90                  95

Ile Ala Gln Phe Leu Tyr Lys Gly Glu Gly Leu Asn Lys Thr Ala Ile
                100                 105                 110

Gly Asp Tyr Leu Gly Glu Arg Asp Glu Phe Asn Ile Gln Val Leu His
            115                 120                 125

Ala Phe Val Glu Leu His Glu Phe Thr Asp Leu Asn Leu Val Gln Ala
            130                 135                 140

Leu Arg Gln Phe Leu Trp Ser Phe Arg Leu Pro Gly Glu Ala Gln Lys
145                 150                 155                 160

Ile Asp Arg Met Met Glu Ala Phe Ala Gln Arg Tyr Cys Gln Cys Asn
                165                 170                 175

Asn Gly Val Phe Gln Ser Thr Asp Thr Cys Tyr Val Leu Ser Phe Ala
                180                 185                 190

Ile Ile Met Leu Asn Thr Ser Leu His Asn Pro Asn Val Lys Asp Lys
            195                 200                 205

Pro Thr Val Glu Arg Phe Ile Ala Met Asn Arg Gly Ile Asn Asp Gly
    210                 215                 220

Gly Asp Leu Pro Glu Glu Leu Leu Arg Asn Leu Tyr Glu Ser Ile Lys
225                 230                 235                 240

Asn Glu Pro Phe Lys Ile Pro Glu Asp Asp Gly Asn Asp Leu Thr His
                245                 250                 255

Thr Phe Phe Asn Pro Asp Arg Glu Gly Trp Leu Leu Lys Leu Gly Gly
                260                 265                 270

Gly Arg Val Lys Thr Trp Lys Arg Arg Trp Phe Ile Leu Thr Asp Asn
            275                 280                 285

Cys Leu Tyr Tyr Phe Glu Tyr Thr Thr Asp Lys Glu Pro Arg Gly Ile
            290                 295                 300

Ile Pro Leu Glu Asn Leu Ser Ile Arg Glu Val Glu Asp Ser Lys Lys
305                 310                 315                 320
```

-continued

```
Pro Asn Cys Phe Glu Leu Tyr Ile Pro Asp Asn Lys Asp Gln Val Ile
            325                 330                 335

Lys Ala Cys Lys Thr Glu Ala Asp Gly Arg Val Val Glu Gly Asn His
            340                 345                 350

Thr Val Tyr Arg Ile Ser Ala Pro Thr Pro Glu Glu Lys Glu Glu Trp
            355                 360                 365

Ile Lys Cys Ile Lys Ala Ala Ile Ser Arg Asp Pro Phe Tyr Glu Met
    370                 375                 380

Leu Ala Ala Arg Lys Lys Lys Val Ser Ser Thr Lys Arg His
385                 390                 395
```